United States Patent  
Gloger

(10) Patent No.: US 9,335,275 B2  
(45) Date of Patent: May 10, 2016

(54) DEVICE AND METHOD FOR IDENTIFYING ANOMALIES ON INSTRUMENTS

(71) Applicant: Karl Storz GmbH & Co. KG, Tuttlingen (DE)

(72) Inventor: Oliver Gloger, Berlin (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 589 days.

(21) Appl. No.: 13/650,751

(22) Filed: Oct. 12, 2012

(65) Prior Publication Data

US 2013/0093877 A1    Apr. 18, 2013

(30) Foreign Application Priority Data

Oct. 13, 2011  (DE) .......................... 10 2011 054 448

(51) Int. Cl.
- *H04N 7/18* (2006.01)
- *G01N 21/94* (2006.01)
- *G01N 21/88* (2006.01)
- *A61B 19/00* (2006.01)

(52) U.S. Cl.
CPC ............ *G01N 21/94* (2013.01); *G01N 21/8851* (2013.01); *A61B 19/44* (2013.01)

(58) Field of Classification Search
CPC .......... H04N 13/0422; H04N 1/00002; H04N 1/00031; H04N 1/00045
See application file for complete search history.

(56) References Cited

U.S. PATENT DOCUMENTS

| 6,653,146 | B1* | 11/2003 | Ruvinsky et al. ............. 436/172 |
| 7,180,014 | B2* | 2/2007 | Farber et al. ................ 177/25.19 |
| 7,997,847 | B2* | 8/2011 | Treat ...................... A61B 19/02 356/237.1 |
| 2005/0038556 | A1 | 2/2005 | Gagnon et al. |
| 2005/0119783 | A1 | 6/2005 | Brisson et al. |
| 2006/0008866 | A1* | 1/2006 | Flick et al. ...................... 435/34 |
| 2009/0317002 | A1* | 12/2009 | Dein ...................... A61B 19/44 382/224 |
| 2010/0276344 | A1* | 11/2010 | Yamada et al. ................ 209/552 |
| 2011/0032349 | A1 | 2/2011 | Calonge San Matias et al. |
| 2011/0117025 | A1* | 5/2011 | Dacosta et al. ................. 424/9.6 |

FOREIGN PATENT DOCUMENTS

DE    202011050001 U1    7/2011

* cited by examiner

*Primary Examiner* — Andy Rao  
*Assistant Examiner* — Tyler Edwards  
(74) *Attorney, Agent, or Firm* — Whitmyer IP Group LLC

(57) ABSTRACT

The present invention relates to a device for identifying anomalies on medical instruments, having a data processing installation and an instrument analyzing unit. The data processing installation has a display unit, a database, a first interface and an evaluation unit and the instrument analyzing unit has a support and at least one camera. The at least one camera is arranged and oriented such that it can capture image data from medical instruments arranged on the support from at least one perspective, and the data processing installation is designed such that it uses the first interface to receive image data from the at least one camera and can store the received image data in the database. Further, it can use the evaluation unit to examine said image data for regions which have anomalies. In addition, the invention also relates to an according method.

11 Claims, 8 Drawing Sheets

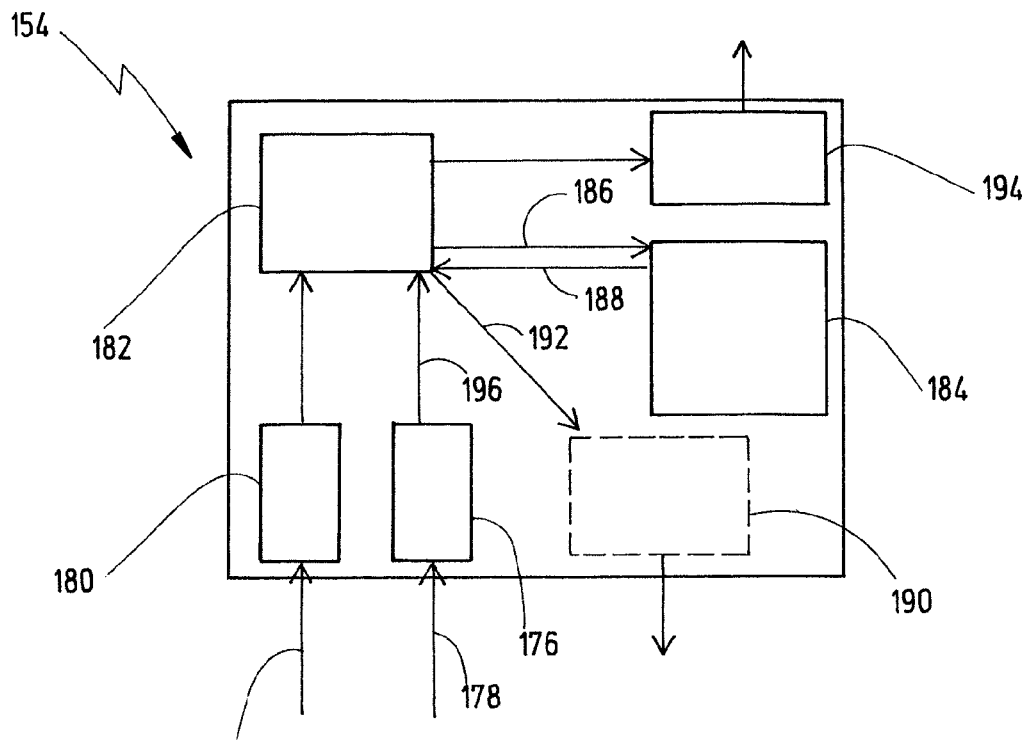
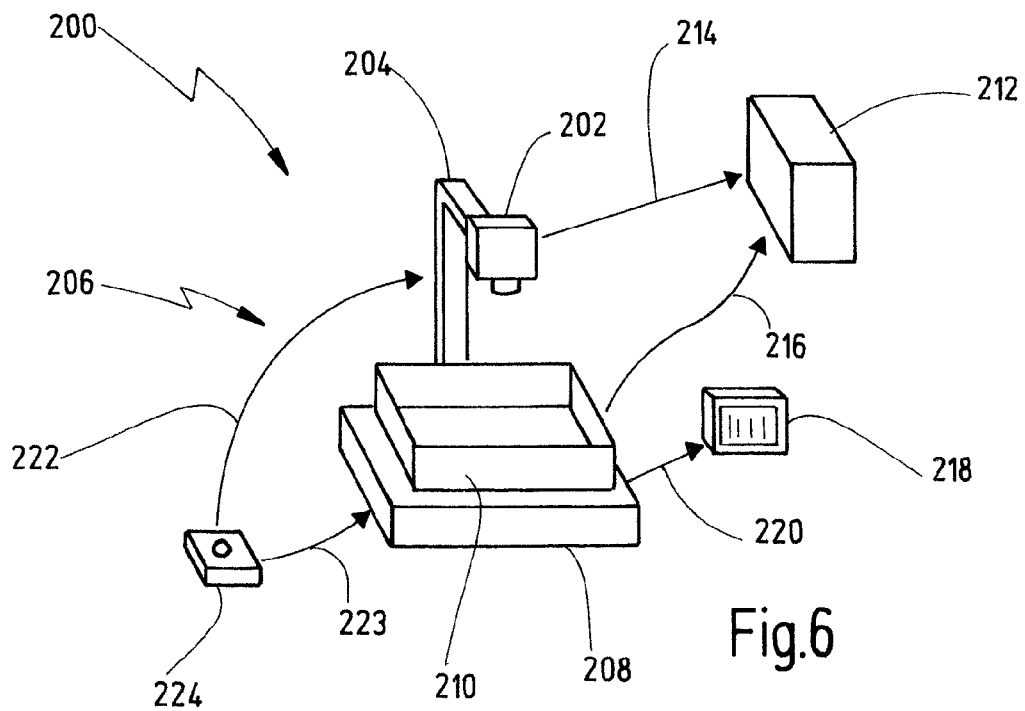

DEVICE AND METHOD FOR IDENTIFYING ANOMALIES ON INSTRUMENTS

BACKGROUND OF THE INVENTION

The present invention relates to a device and a method for identifying anomalies on medical instruments.

Reusable medical instruments are frequently exposed to conditions that are detrimental to materials as a result of the harsh conditions during cleaning and sterilization (action of chemicals, high temperatures, etc.) and the high turnover. In addition, the medical instruments must be quickly ready to use again, which means that a thorough examination of the instruments before an operation is often counter productive since it is linked to a high level of time involvement. Since a thorough examination also requires the employment of specialized personnel, it simultaneously also has an adverse effect on total costs.

Possible faults or anomalies on such instruments may be organic residues from previous operations, for example. Should these come into contact with the respectively subsequent patients during subsequent operations, this can result in infections.

Similar problems are also posed by damage to the medical instruments. This may involve anomalies such as damage or defects in the form of corrosion and/or fractures, for example. Besides the risks of infection that are also linked to such anomalies, they also pose a threat of injury if such an instrument breaks in the process of an operation, for example.

Within the present invention the term "anomaly" is intended to be understood to mean any unusual coating on the instrument or any unusual change in the material of the instrument that can be identified on the outside, albeit only faintly and possibly without being visible to the human eye. Examples that may be mentioned in this context are soiling, such as organic residues or residues of cleaning agents, and damage to the material, such as factory faults or damage as a result of fractures, cracks, corrosion, substantial scratches that impair function, and the like, for example.

Risks of infection and injury of the aforementioned type must be avoided by all means. On the other hand, cost and time-saving considerations have priority more and more frequently today. Particularly in the area of cleaning and sterilization of instruments, it is more and more often the case that hospitals hand this work to external service providers. However, these are not always able either to employ qualified personnel or to provide the latter at least with the appropriate time for the necessary checks in order to be able to work cost effectively. This then again results in disadvantages for the quality of the cleaning and/or sterilization.

U.S. Pat. No. 7,997,847 B2 describes systems and methods for processing a plurality of surgical instruments for cleaning and/or packaging. Therein, the surgical instruments are identified and oriented according to type and using an automated apparatus. Further, specialized tools are provided for automatically opening and closing surgical instruments, flipping instruments and assisting in the processing and maintenance of surgical instruments. Instruments may further be inspected for cleanliness via machine vision using image comparison with stored images resulting in an information about the possibility of contamination in general. The provided information is therefore limited to the mere possibility of the existence of a contamination. No information is achieved about the kind or amount of contamination.

SUMMARY OF THE INVENTION

The present invention is based on the object of providing a device and a method which allow instruments to be examined and monitored for the aforementioned anomalies effectively, quickly, reliably and in a cost-saving fashion. Further, a classification of the anomalies should be possible.

This object is achieved according to a first aspect of the present invention by a device for identifying anomalies on medical instruments, with:
  a data processing installation and
  an instrument analysing unit;
    the data processing installation having:
      a display unit,
      a database,
      a first interface, and
      an evaluation unit; and
    the instrument analysing unit having:
      a support and
      at least one camera,
  wherein the at least one camera is arranged and oriented such that it can capture image data from medical instruments arranged on the support from at least one perspective, and
  wherein the data processing installation is designed such that
    it uses the first interface to receive image data from the at least one camera,
    it can store the received image data in the database,
    it can use the evaluation unit to examine the image data for regions which may have anomalies,
    it can classify the regions, and
    it can use the classification to determine whether the regions are respectively a regular part of the respective medical instrument or an anomaly,
  wherein the anomalies are preferably damage or soiling.

Such a device advantageously allows a data processing installation and image analysis in an appropriate instrument to be used to quickly perform an examination for such anomalies. The latter can even be identified without a relatively high level of time and effort if they involve small areas which are not at all or barely identifiable by the human eye. By way of example, it is therefore possible to identify a fine crack comparatively quickly. It is therefore also possible to identify incipient corrosion that is initially still minor.

Besides the examination of individual instruments, this invention preferably also provides for a plurality of instruments to be placed onto the appropriate support at the same time and hence to be able to be examined for anomalies by the device according to the invention simultaneously. This is linked to a distinct time saving. By way of example, it thus allows an entire set of instruments to be examined as appropriate following assembly and prior to sterilization.

Furthermore, this device can be connected to other methods which are performed by using data processing installations and are related to the cleaning, sterilization and organization of such medical instruments. An example that may be mentioned for such a method in this case is the assembly of sets of instruments by using data processing installations. This can be accomplished with a device which has a similar design. Thus, this may also involve the instruments that are intended to be packed together to form such a set of instruments being arranged on such a support. During this placement of the instruments on the support, the device according to the invention can then examine the respective instruments for anomalies at the same time or shortly before or afterwards.

Further, the storage of the image data and also of the analysis results in the database has the advantage that such examination of the instruments using data processing installations makes it a simple matter to obtain an overview of which instruments are frequently observed to have which anomalies. The data received in this manner allow a conclusion to be drawn, without relatively great complexity, as to where any faults in the cleaning and sterilization process are and also as to which cleaning and sterilization processes might be unsuitable for which instruments. By way of example, the recurring occurrence of corrosion on a plurality of or all instruments of one type thus makes it possible to conclude that, by way of example the cleaning agent used is too aggressive. In addition, it is even possible for cracks or fractures discovered, which have also become conspicuous as a result of incipient corrosion, for example, to also permit a conclusion that cleaning or sterilization apparatuses have malfunctioned. This is the case, by way of example, when the instrument always strikes a wall or another component of the apparatus or else another instrument in the respective apparatus, e.g. because one of the instruments involved is not being held correctly.

This embodiment has the further advantage that it increases the effectiveness of the device. Thus, dividing the anomalies into particular classes allows the data processing installation to quickly make an association as to whether the identified alleged anomaly, i.e. primarily the deviation from the usual instrument nature, is a regular part of the instrument or an anomaly within the meaning of soiling or damage.

If it is a regular part of the instrument, the device is able to identify this by comparing it with the classes for such deviations resulting from instrument parts. By way of example, this may be the case when there is a plastic grip on instruments which are actually metal, for example. In that case, the device does not otherwise need to report a fault or take further measures. In the case that soiling or damage is present either an according warning can be provided to a user or this incident can be recorded for later examinations or processing.

The correspondingly required classes which the device according to the present invention, particularly the data processing installation, uses for the comparisons with the classified anomalies may initially have been provided in the system by the manufacturer. Preferably, however, the classes are created for each group of instruments individually in order to achieve as high a success rate as possible from the device according to the present invention. To this end, the device according to the invention points out previously unknown and unclassified anomalies to the user when they arise and allows the anomalies to be grouped or associated with a type of damage or soiling, i.e. with a class of anomalies. Alternatively, the system can in this case then also be instructed that what is allegedly an anomaly is actually a part of the instrument rather than an anomaly that involves damage or soiling.

This previously described type of learning in the device has the advantage that even when new instruments, which have not been used previously and are therefore of unknown type, are included the device can continually adapt to changes and freshly added instruments and instrument types and can continue to learn.

In the basic case, the device can also examine new or unknown instruments without further learning, however. The reason for this is that the alleged anomalies, that is to say the damage, soiling and also the instrument parts, are classified and are stored in the data processing installation. Preferably, therefore, no comparison with reference images of all possible instruments takes place in which, by way of example, faults are identified by virtue of an actual state differing from a nominal state. In contrast to the present invention, this would necessitate storage for each instrument used and for each of the subclasses and sizes associated with said instrument. The identification of and examination for anomalies using the classes thereof therefore works irrespective of the instruments that are actually present, particularly of the precise types and sizes thereof. This is the case particularly when the instruments are made from the same materials, such as medical steel.

According to an embodiment of the device according to the present invention, the data processing installation is also designed such that it can use the classification to indicate the type of anomaly.

If it is an anomaly that involves damage or soiling, this embodiment subsequently allows determination of the class to make an association with the type of anomaly. In such a case, the device is then able either to communicate the type of anomaly to the user or even to take appropriate measures straightaway. In this context, measures mean the automatic removal by the device, for example, which involves a damaged instrument being rejected completely or removed for repair, for example. In the case of soiling, removal would be such that the affected instrument is subjected to a further cleaning and sterilization cycle, for example.

According to another embodiment of the device according to the present invention, the data processing installation is designed such that the examination for and finding of anomalies takes place using colour information from the image data.

This embodiment has the advantage that it allows the examination to be accomplished using a property that is easily accessible from the image data. On account of the nature of the medical instruments with their generally metallic surface and black plastic parts, changes in colour are easily and quickly identifiable deviations or anomalies. It is therefore possible to dispense with computation-intensive and time-consuming types of object identification as an alternative refinement for identifying anomalies.

According to another embodiment of the device according to the present invention, the support has a contrast-enhancing background.

This embodiment has the advantage that the evaluation unit of the data processing installation can thus distinguish the instrument to be examined from the background with a significantly higher success rate and level of effectiveness. The colour and image information from the background can easily be separated from the relevant information.

According to another embodiment of the device according to the present invention, the camera is arranged such that a position thereof can be altered, as a result of which it can capture the image data from at least two perspectives.

The term "perspective" as used within the context of the present invention refers to the orientation of a respective camera in relation to a respective instrument in terms of angle of azimuth and polar angle. In this context, a change in the perspective results in a change in this orientation by virtue of at least one of these two angles, which, together with the distance to the origin of a spherical coordinate system, explicitly determine the position of an object in such a system, being altered.

This embodiment has the advantage that the image data from the instruments can be identified not just from a single fixed perspective. Consequently, this has the advantage that, particularly in the case of relatively complex instruments, these too can be examined for anomalies from a plurality of sides.

Preferably, the position of the camera can, to this end, be altered in a motor-driven fashion, even more preferably altered automatically, by virtue of the motors being able to be actuated by the data processing installation.

Furthermore, this has the advantage that the image data can be captured from a plurality of perspectives automatically in one pass and the data processing installation can thus quickly perform and conclude the examination for anomalies without further action from a user.

According to another embodiment of the device according to the present invention, the support has a transparent base area, and the contrast-enhancing background is arranged such that a position thereof can be altered between the two sides of said transparent base area.

This embodiment has the particular advantage that a medical instrument which is arranged on the transparent base area can therefore have the image data captured from above as well as from below.

This merely requires the contrast-enhancing background to be arranged firstly below the transparent base area and in the next step above the transparent base area. In other words, the contrast-enhancing background is always arranged on the back of the medical instrument to be detected, in relation to the camera perspective.

A camera that can have the camera perspective positioned in an alterable fashion can then also be used, possibly in a motor-driven and automated fashion, to capture image data from below the transparent base area from the medical instrument.

To this end, the contrast-enhancing background is preferably arranged so that it can be automatically altered.

According to another embodiment of the device of the present invention, the support has a transparent base area, and the device comprises two contrast-enhancing backgrounds respectively arranged on opposite sides of the transparent base area, such that at least one contrast-enhancing background is arranged behind a medical instrument arranged on the support with respect to a respective perspective of the at least one camera.

In this embodiment a respective contrast-enhancing background is provided on each side of the transparent base area. Accordingly, this embodiment has the same advantages as the previously mentioned embodiment, i.e. that a medical instrument which is arranged on the transparent base area can have the image data captured from above as well as from below. Therefore, at least one contrast-enhancing background is always arranged on the back of the medical instrument to be detected, with respect to the camera perspective. In contrast to the previous embodiment, no rearrangement of the contrast-enhancing background is necessary. This embodiment is especially beneficial in embodiments where two cameras are used for the fine identification unit which are arranged on opposite sides of the transparent base area. This allows a simultaneous capturing of the image data by both cameras and, therefore, saves a lot of time Alternatively, the device according to the invention preferably has at least one further camera, with at least one camera being arranged on each side of the transparent base area and being arranged and oriented such that it can capture image data from the instruments arranged on the support from at least one perspective, the perspective of one camera being directed onto the support from above and that of the further camera being directed onto the support from below the transparent base area.

This embodiment has the advantage that, particularly in combination with the additional automatically alterable positionability of the respective camera, image data from the respective instruments can therefore be captured completely automatically from all possible perspectives. This then allows all outwardly identifiable anomalies in the medical instruments to be detected.

The object of the present invention is further achieved according to another aspect of the present invention by a method for identifying anomalies on medical instruments with a device for identifying anomalies on medical instruments, with:
 a data processing installation and
 an instrument analysing unit;
  the data processing installation having:
   a display unit,
   a database,
   a first interface, and
   an evaluation unit; and
  the instrument analysing unit having:
   a support and
   at least one camera,
 wherein the at least one camera is arranged and oriented such that it can capture image data from medical instruments arranged on the support from at least one perspective, and
 wherein the data processing installation is designed such that
  it uses the first interface to receive image data from the at least one camera,
  it can store the received image data in the database,
  it can use the evaluation unit to examine the image data for regions which may have anomalies,
  it can classify the regions, and
  it can use the classification to determine whether the regions are respectively a regular part of the respective medical instrument or an anomaly;
the method comprising the following steps:
 a) placing at least one instrument onto the support of the instrument analysing unit,
 b) capturing image data by the at least one camera,
 c) forwarding the image data to the data processing installation,
 d) analysing the image data for anomalies on the instrument and
 e) communicating information about the anomalies to a user.

Contrary to the previously customary procedure, this method has the advantage that the user now does not have to painstakingly scan the instruments himself, which is time-consuming and cost-intensive, as already mentioned previously, but instead the user in this case merely needs to place the instruments onto the support of the instrument analysing unit. As a result, the device then uses this method to provide the user with the information regarding whether anomalies on the instruments have been discovered. Further, the user may be provided with additional information regarding the anomalies per se, like but not limiting to position, kind of anomaly, size etc.

Otherwise, the advantages are evident from the comments which have been made previously in connection with the device.

According to an embodiment of the method according to the present invention, step d) of said method comprises the following steps:
 aa) finding regions of conspicuous colour,
 bb) classifying the regions of conspicuous colour, and
 cc) using the classification to determine whether the region of conspicuous colour is a regular part of the instrument or an anomaly,
wherein the method preferably further comprises the following step in step d):
 dd) determining the type of anomaly in the region of conspicuous colour.

This embodiment of the method has the advantage that the step of finding regions of conspicuous colour looks for a feature in the image data which is characteristic of the respective anomalies. By way of example, patches of rust typically have a comparatively large red component which deviates from the usual instrument colour. In the present case, this is additionally benefited by virtue of the instruments being metallic and otherwise usually having only black plastic parts. Both metallic, that is to say grey-white, and black are clearly distinguished from the colours of the anomalies in terms of the image data.

The classification and determination of the type of anomaly using the classification has, as already explained previously, the advantage that it is thus firstly possible to provide simple references and, moreover, there is also an efficient method for comparing the identified anomalies with these references. In this context, this method otherwise involves only learning the classes. As has already been explained previously, it is not necessary to store references for new instruments and instrument types when they are used.

Particularly, in the preferred embodiment, this furthermore results in it thus being a simple matter to associate and hence identify the anomalies. Besides the categorization of the anomaly either as a regular part of the instrument or as an anomaly that involves damage or soiling, it is therefore also possible, in the latter case, to make a precise association with the type of damage or soiling.

This can then be communicated to the user, as a result of which he takes further steps. Alternatively, in one preferred embodiment, it is also conceivable for the method according to the invention also to involve the medical instruments that are identified with an anomaly being removed straightaway. In this way, soiled instruments can be removed for the purpose of a further cleaning cycle, while damaged and faulty instruments can be removed completely or for repair, depending on the type of damage.

Preferably, steps cc) and dd) are implemented by comparisons of the ascertained class for the region of conspicuous colour with already known classes for anomalies and instrument parts.

This has the advantage that the data that have been learned are also drawn on in this case.

According to another embodiment of the method according to the present invention, step aa) has the following steps:
  determining a colour intensity of each pixel,
  comparing the colour intensity with a predetermined threshold value,
  categorising a respective pixel as being of conspicuous colour if the threshold value is exceeded,
  combining all adjacent pixels of conspicuous colour to form a region of conspicuous colour,
wherein determining the colour intensity of each pixel is preferably implemented by ascertaining the difference of the image channel values of the individual image channels.

The term "pixels" as used within the context of the present invention is intended to be understood to mean the smallest unit of a digital raster graphic system, according to the general definition. In this context, it can be assumed that, within the meaning of the present invention, the received image data are available in the form of raster graphics.

In addition, such a pixel can be understood to mean the smallest unit with data which preferably have colour information. This colour information is based on a certain colour space according to the image data, particularly according to the format thereof. In this case, it is assumed for the description of the present invention, by way of example, that the colour space for such a pixel which is used for the explanations herein is the RGB colour space. However, this assumption is made only for the purpose of simplified explanation so as not to repeat the comments made in relation to one colour space for all possibly conceivable and existing other colour spaces in each case. The use of the RGB colour space should therefore not be understood to be a limitation in this context. Hence, other known colour spaces are also conceivable within the context of this invention, such as the XYZ, I1I2I3, YUV or YCbCr colour space, to name but a few known and established colour spaces. In addition, it is also conceivable for a dedicated colour space to be developed or stipulated specifically for the present method.

The previously mentioned embodiment of the method according to the present invention has the advantage that the feature of the colour intensity is well suited, in a first step, to first of all check whether there are any generally significant colour conspicuousnesses. In this context, the term "colour intensity" is intended to be understood to mean that this involves the presence of colour information of any type that contrasts with uncoloured information, such as white, grey and black. In a first step, the colour intensity is therefore not limited to individual particular colours. Within the context of this invention, there is therefore a higher colour intensity as soon as there is a deviation from the typical instrument colours. In line with the comments made previously, these are metallic white to grey and normally black for respective plastic parts.

The provision of a threshold value has, furthermore, the advantage that the sensitivity of the method can thus be adjusted to suit the desired requirements. Lowering the threshold value therefore results in higher sensitivity, while raising the threshold value decreases the sensitivity. In the latter case, only regions of distinctly conspicuous colour would thus be identified.

Furthermore, the combination of all adjacent pixels of conspicuous colour to form a region of conspicuous colour has the advantage that the latter can thus easily be presented to the user. This is preferably accomplished by output on a display unit of a device on which this method is being performed.

Determining the colour intensity using the difference of the image channel values of the individual image channels is a simple way of taking the available colour information from a pixel and, without complex calculations, obtaining information about whether or not the relevant pixel belongs to a region of conspicuous colour. The reason for this is that, distinctly for the aforementioned colours white, grey and black, all image channel values of a pixel are close to one another, whereas for other colours at least one image channel value of a pixel deviates distinctly from the other image channel values. This means that it is thus possible to identify a deviation from the cited typical instrument colours.

According to another embodiment of the method according to the present invention, step bb) comprises the following steps:
  ascertaining a probability for each pixel in a region of conspicuous colour of belonging to a particular class of anomalies,
  selecting the class having the highest probability and assigning this class to the respective pixel, and
  selecting the most frequently occurring class among the total number of all pixels in the region of conspicuous colour and assigning this class to the region of conspicuous colour.

The ascertainment and assignment of a particular class to a respective pixel using the probabilities has the significant advantage that the method according to the invention is thus capable of learning. This is evident from the fact that the probabilities are not fixed, but rather are variable and alterable. This is preferably implemented in the form that a separate learning method is possible either first of all at the outset or at any time during the operation of a device using the method according to the present invention. This learning method then accordingly involves the capture of image data from medical instruments that have anomalies. These image data are examined for anomalies in line with the method according to the present invention. If an anomaly is discovered in this process, the user can assign this anomaly to a particular class, either of regular instrument parts or damage or soiling. On the basis of these data, probabilities are then ascertained, on the basis of which a probability of the ascertained colour information belonging to the respective classes is ascertained for each pixel using the colour information and in relation to each available class.

Besides an explicit learning phase, it is furthermore also conceivable and possible for the user to act at any time during the performance of the method according to the present invention if he identifies that an association with a class is incorrect. This then also adjusts the relevant probability values.

The remaining steps with the selection and assignment of the class having the highest probability to the respective pixel and the selection of the most frequently occurring class among the pixels of the region of conspicuous colour and the assignment of this class to the region of conspicuous colour then advantageously result in the conspicuous region ultimately being assigned the class to which the cause of the colour conspicuousness belongs.

Further, this invention relates to a computer program comprising program code means which, when carried out on a computer, cause a computer to carry out the steps of the method according to the present invention.

According to another aspect of the present invention, a non-transitory computer-readable recording medium is provided that stores therein a computer program product, which, when executed by a processor, causes the method according to the present invention to be performed.

A computer program may be stored/distributed on a suitable medium, such as an optical storage medium or a solid-state medium supplied together with or as parts of other hardware, but may also be distributed in other forms, such as via the Internet or other wired or wireless telecommunication systems.

It goes without saying that the features cited above and those still to be explained below can be used not only in the respectively specified combinations but also in other combinations or on their own without departing from the scope of the present invention.

BRIEF DESCRIPTION OF THE DRAWINGS

The invention is described and explained in more detail below using a few selected exemplary embodiments in connection with the appended drawings, in which:

FIG. 5 shows a schematic representation of a data processing installation for a device as shown in FIG. 4, FIG. 6 shows a schematic perspective representation of a coarse identification unit with a camera and a scale.

DESCRIPTION OF PREFERRED EMBODIMENTS

Figure 1:
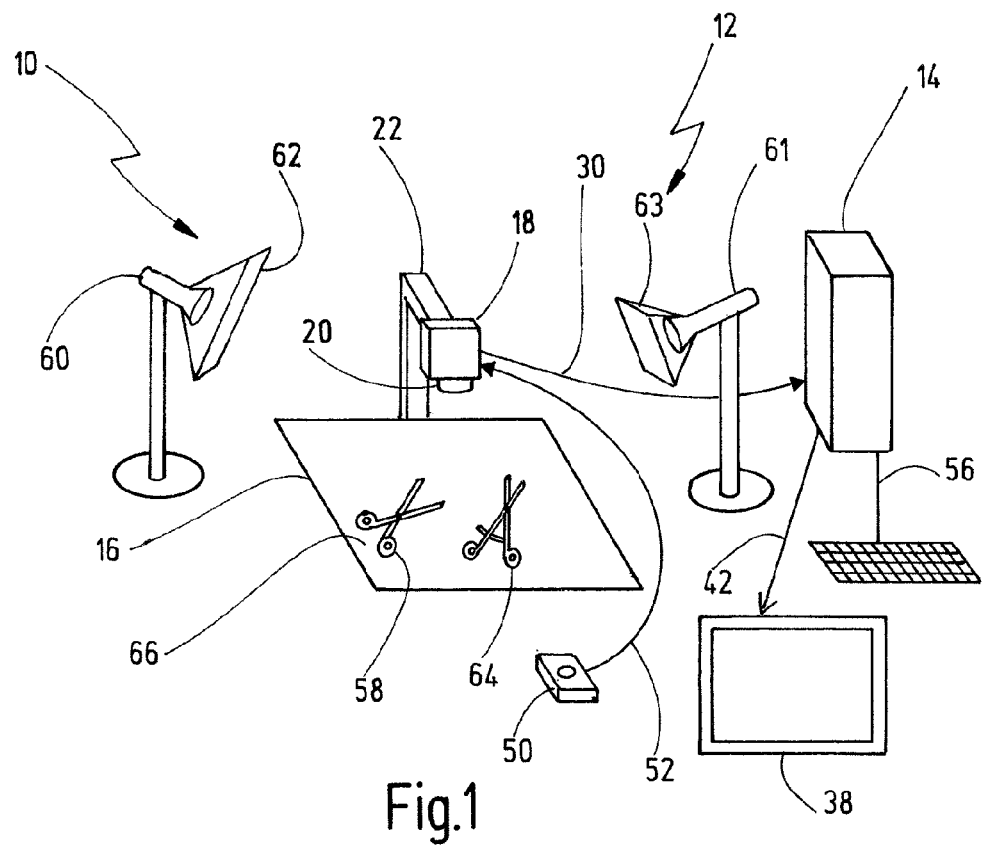
FIG. 1 shows a schematic perspective representation of a device according to the present invention with an instrument analysing unit.

The devices according to the present invention that are shown and described below are denoted by the reference numerals 10, 100, 150, 300, 350 and 370.

The device 10 according to the invention which is shown in FIG. 1 has an instrument analysing unit 12 and a data processing installation 14. The instrument analysing unit 12 has a support 16 and a first camera 18.

The first camera 18 is arranged above the support 16 such that the lens 20 thereof, and hence accordingly the perspective thereof, is directed onto the support 16. To this end, the first camera 18 is arranged above the support 16 with reference to the illustration in FIG. 1 by means of a stand 22.

Figure 2:
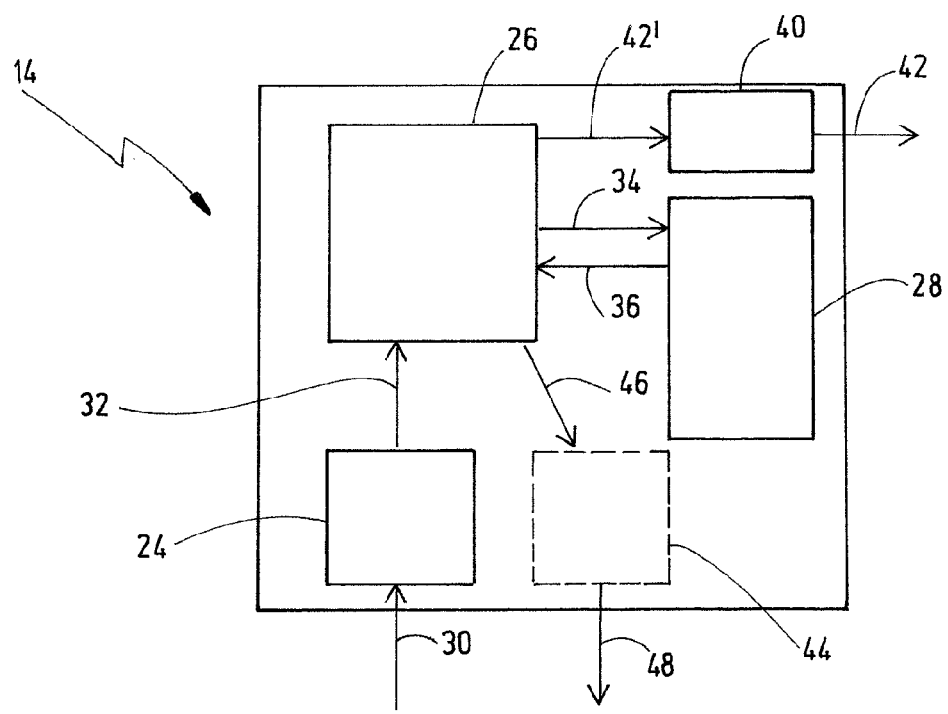
FIG. 2 shows a schematic representation of the configuration of a data processing installation according to the present invention.

The data processing installation 14 for its part has a first interface 24, an evaluation unit 26 and a database 28, as can be seen in FIG. 2. The first interface 24 connects the data processing installation 14 to the first camera 18 and said data processing installation 14 uses this first interface 24 to receive image data from the first camera 18. This is indicated schematically in FIGS. 1 and 2 by an arrow 30. The image data received in this manner are then forwarded from the first interface 24 to the evaluation unit 26. This is indicated schematically by an arrow 32. The evaluation unit 26 can now directly begin to evaluate and analyse the image data received in this manner, or can store the data in the database 28 first of all. This is indicated by an arrow 34. For the purpose of evaluating the data in the evaluation unit 26, the latter requires information regarding classes of anomalies, as described in more detail below. The evaluation unit 26 likewise receives this information from the database 28, as indicated schematically by an arrow 36.

Once the evaluation unit 26 has ascertained an evaluation result, said result is forwarded to a display unit 38. This can be accomplished by means of a separate connection 40 on the data processing installation 14 and is otherwise indicated schematically by arrows 42 and 42'. Various configuration options can be considered for such a display unit 38. Thus, it is firstly conceivable to design specific display units for the intended purpose and to integrate them into the data processing installation 14. Otherwise, it is alternatively conceivable to use an ordinary computer monitor for this purpose, said computer monitor being able to be controlled by means of the connection 40.

Besides or in addition to the described option of outputting the evaluation data on the display unit 38, it is also conceivable for the data processing installation 14 furthermore to have a control unit 44. This is shown as an optional element in FIG. 2 by means of dashed lines. The control unit 44 can receive data from the evaluation unit 26, as indicated schematically by an arrow 46, and can then use said data to control external appliances or devices directly or indirectly. This is likewise indicated schematically by an arrow 48. Examples of such devices are robots, which are not shown in more detail here, however.

In order to achieve triggering of the image capture by the first camera 18, the device 10 also contains a push-button 50. This push-button 50 is functionally connected to the first camera 18. This is indicated schematically by means of an arrow 52. In order to otherwise allow further communication between a user and the device 10, the latter also has a keyboard 54 which is connected to the data processing installation 14. This is indicated schematically by means of a connecting line 56.

A medical instrument to be examined is shown schematically in FIG. 1 as a pair of scissors 58. This pair of scissors 58 is arranged on the first support 16. Hence, the pair of scissors 58 is beneath the first camera 18. In line with the perspective orientation of this first camera 18, this pair of scissors 58 is captured by the first camera 18 when the image data are captured.

In order to optimize the snapshots or the image capture, the device 10 also has lighting devices. These lighting devices are shown schematically here by lamps 60 and 61. So as also to avoid reflections from the instruments that are to be identified, elements 62 and 63 for diffuse light conditions are also provided. These elements 62 and 63 may be made from special photo card, for example.

The mode of operation of the instrument analysing unit 12 in respect of the capture of the image data will now be explained by way of example with reference to the device 10 and FIGS. 1 and 2.

First of all, a user places the instruments that are to be examined onto the support 16. These are shown here by means of the pair of scissors 58 and a clamp 64 by way of example.

When the instruments have been placed onto the support 16, the image data from these instruments are captured by means of the first camera 18. This can be triggered in one preferred embodiment by the user operating the push-button 50. Alternatively, it is also conceivable for the user to use the keyboard 54 for triggering.

The image data captured by the first camera 18 are now forwarded via the first interface 24 to the evaluation unit 26 in the data processing installation 14. There, these image data are then processed further and analysed in the evaluation unit 26, as described in more detail below.

The result of the examination is then output on the display unit 38.

In this context, it should be mentioned that, for correct examination of the instruments on the support 16, it makes sense to arrange the instruments such that they do not overlap one another.

In order to optimise the capture of the image data, so that the relevant examination provides the best possible results, it is advisable to ensure good lighting and contrast conditions.

To this end, the support 16 may be designed to have a contrast-enhancing background 66. This can easily be implemented, by way of example, by virtue of the support 16 having an even colouring, e.g. blue.

In addition, the lamps 60 and 61 should provide intense lighting of the support 16 and at the same time ensure the most diffuse light possible, by virtue of the elements 62 and 63, in order to reduce undesirable reflections.

Figure 3:
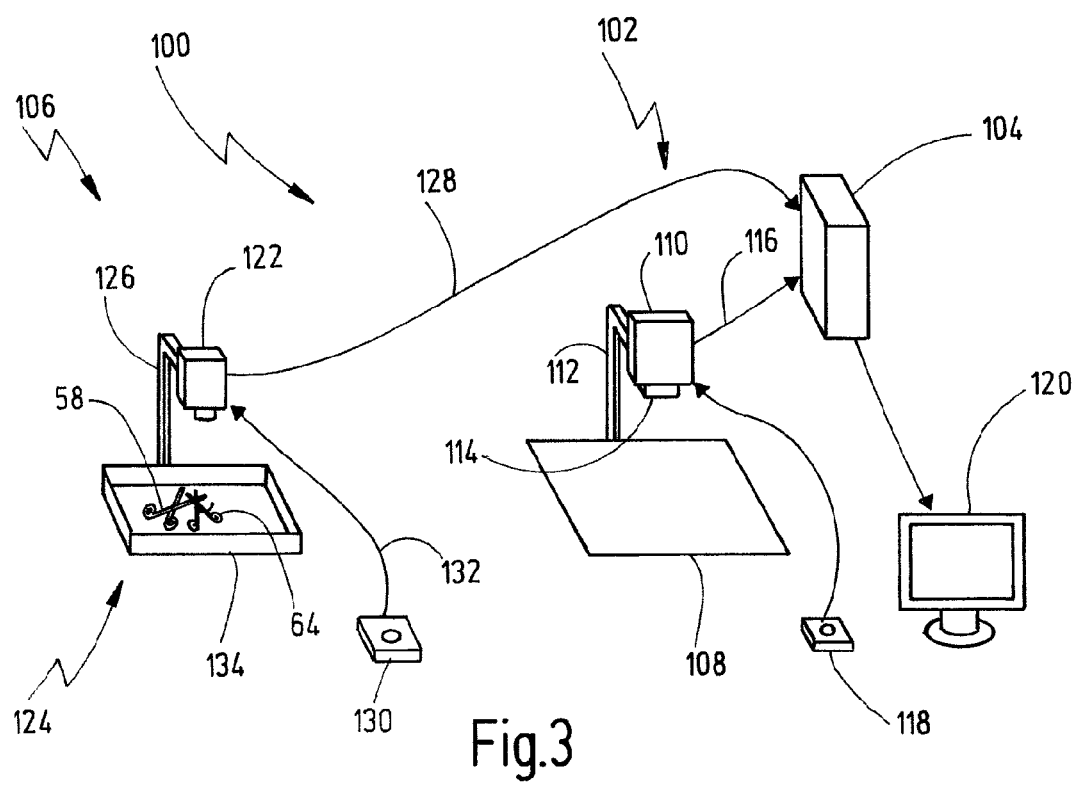
FIG. 3 shows a schematic perspective representation of a further device according to the present invention with a combination of instrument analysing unit and coarse identification unit, the latter having a camera.

FIG. 3 shows a further device 100 according to the present invention.

This device 100 has an instrument analysing unit 102, a data processing installation 104 and a coarse identification unit 106.

The data processing installation 104 is designed in the manner of the data processing installation 14 and is not shown in more detail below. Instead, reference is made to the previous comments. The instrument analysing unit 102 has a support 108 and a first camera 110. In this case, the first camera 110 is arranged on a stand 112. This allows it to be oriented such that its lens 114 is aiming at the support 108. The first camera 110 shown in this case therefore has the same perspective as the camera 18 from FIG. 1.

The first camera 110 likewise forwards the captured image data to the data processing installation 104, as indicated by the arrow 116. The capture of the image data can be triggered by a push-button 118 in the same way as in the case of the device 10 from FIG. 1. For the purpose of further communication between the user and the device 100, the data processing installation 104 also has a display unit 120. The remaining features and the mode of operation of the instrument analysing unit 102 together with the data processing installation 104 are identical, in principle, to the features and mode of operation of the instrument analysing unit 12 together with the data processing installation 14 of the device 10, for which reason reference is also made in this regard to the explanations made before.

For the purpose of improved illumination and optimization of the contrast ratio between instruments placed on the first support 108, a contrast-enhancing background can likewise be used in this case, in the same way as intense lighting means are used. However, these are not shown in more detail in this case for the purpose of clarity.

The additional coarse identification unit 106 of the device 100 has a further camera 122. This further camera 122 is arranged above a second support 124 in a similar fashion to the first cameras 110 and 18 described before. To this end, it is mounted on a stand 126. The further camera 122 is likewise connected to the data processing installation 104 via a third interface—not shown in more detail in this case. This is indicated schematically by the arrow 128. So as to be able to have image data capture controlled by the user in the case of the coarse identification unit 106 too, the coarse identification unit 106 likewise has a push-button 130. The push-button 130 is functionally connected to the camera 122 for the purpose of triggering. This is indicated schematically by an arrow 132.

The mode of operation of the device 100 is similar to the mode of operation of the device 10. In this case too, a user first of all places appropriate instruments that are to be examined onto the first support 108 and, in line with the comments made previously in connection with the instrument analysing unit 12 and the data processing installation 14, uses the instrument analysing unit 102 and the data processing installation 104 to examine said instruments for anomalies. Subsequently, the user can then transfer the instruments which have no anomalies, for example, to the second support 124. The resultant state is indicated schematically in FIG. 3 again by the instruments from FIG. 1, namely the pair of scissors 58 and the clamp 64.

If all the instruments are now arranged on the second support 124, the further camera 122 can start the image capture. This can be triggered by the user, preferably using the push-button 130. The image data ascertained in this manner are then—as illustrated by the arrow 128—forwarded to the data processing installation 104, which can then use its evaluation unit to start the evaluation. By way of example, this may then involve checking the completeness of a set of instruments using a packing list that is stored in the data processing installation 104.

In one preferred embodiment, the second support 124 has an instrument tray 134. The instruments from the set of instruments, that is to say in this case the pair of scissors 58 and clamp 64, can be placed into this instrument tray 134 directly when they are transferred from the instrument analysing unit 102. This has the advantage that, following successful coarse identification, the instrument tray 134 can be taken out of the coarse identification unit 106 and thus forwarded directly to cleaning and sterilization.

Since the available space in such an instrument tray 134 is usually smaller than the space available on the first support 108 or 16, for example, the instruments to be identified frequently overlap in the coarse identification unit, as is also indicated in FIG. 3 for the pair of scissors 58 and the clamp 64.

So as nevertheless to provide an efficient opportunity to identify the completeness of the instrument set, this situation preferably involves the identification of key features in the image data. By way of example, these key features may have been learnt by the system beforehand or may have been predetermined directly by the user.

A further advantage of the use of key features for identifying the instruments is that the subsequent coarse identification step by the coarse identification unit 106 takes comparatively little time.

The term "key features" as used within the context of the present invention is intended to be understood to mean visual instrument features. These can be automatically predetermined during training on an instrument or else can be calculated using automatic algorithms for each instrument. They are usually conspicuous, prominent and/or highly visible areas of the respective instrument. For this reason, it is also possible for, in particular, an experienced packer or user himself to indicate during training which instrument areas are key features which distinguish them from other instruments of very similar design. These may also be small details, such as small instrument parts, various surface corrugations, indentations, small grooves or the like. Markers or other identifications that have been put on specifically for this purpose are also conceivable. By way of example, key features are alternatively or additionally automatically determined by means of what are known as interest operators, such as the Förstner operator or the Moravec operator.

The use of the coarse identification unit 106 means that the overall device 100 has the advantage that the instrument tray 134 loaded in this fashion is conclusively checked to determine whether the set of instruments is present in full and the instrument tray 134 has therefore been loaded correctly. This precludes faults such as an instrument from a previous provision, e.g. from the instrument analysing unit 102, not being correctly transferred to the associated instrument tray 134, for example.

Besides the option—described previously and illustrated in the comments below—of a separate coarse identification unit in addition to a instrument analysing unit, it is likewise conceivable for this invention to involve the units being combined in terms of design. This would mean that the first and second supports and the first and further (or second and further) cameras are identical. Such an arrangement has a smaller space requirement than a separate arrangement.

Figure 4:
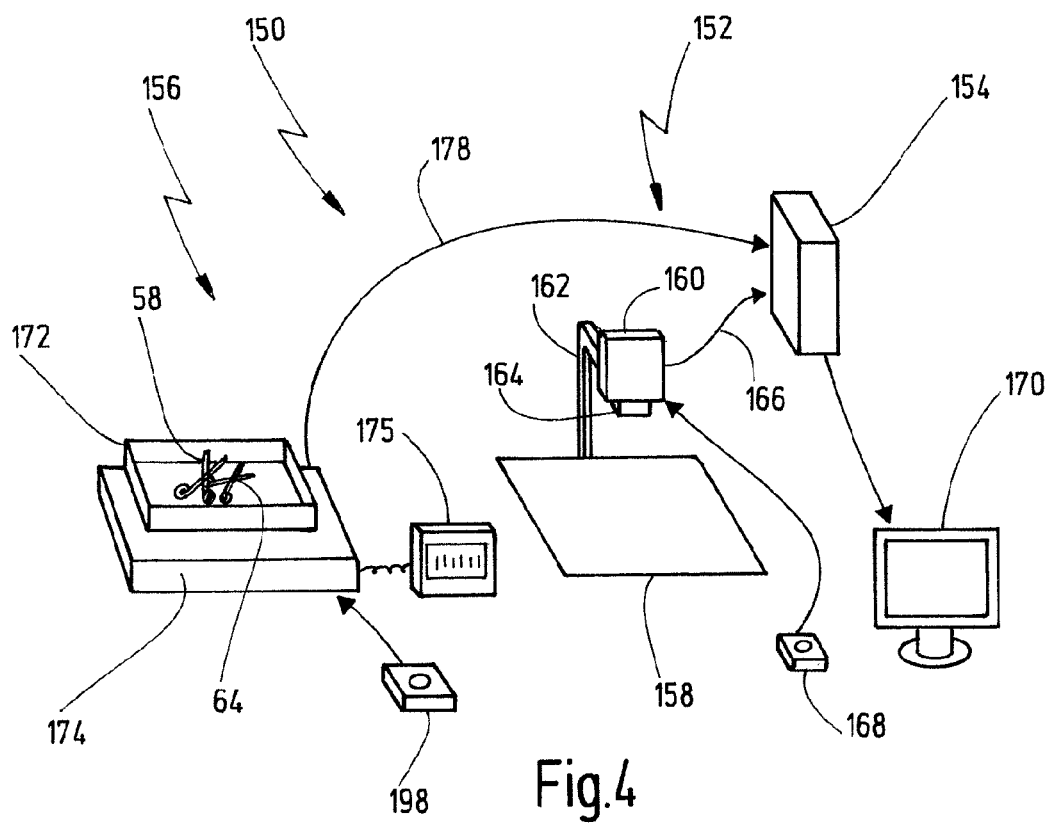
FIG. 4 shows a schematic perspective representation of a further device according to the present invention with a combination of instrument analysing unit with coarse identification unit, the latter having a scale.

FIG. 4 shows a further device 150 according to the present invention.

This device 150 according to the present invention likewise has an instrument analysing unit 152, a data processing unit 154 and a coarse identification unit 156.

In a manner comparable to the devices 10 and 100, the instrument analysing unit 152 has a support 158 and also a first camera 160 with a stand 162 and a lens 164. The first camera 160 is also connected to the data processing installation 154, as indicated by an arrow 166. The first camera 160 can also be triggered by a push-button 168.

The mode of operation of the instrument analysing unit 152 is similar to that of the instrument analysing unit 102, for which reason further explanations are dispensed with here and reference is made only to the previous explanations. A corresponding outcome for the examination of the instruments is then obtained with reference to the set of instruments to be loaded via a display unit 170.

In a manner similarly analogous to the device 100 from FIG. 3, the check on the completeness of an appropriate set of instruments will subsequently involve coarse identification in the coarse identification unit 156.

To this end, the coarse identification unit 156 also has an instrument tray 172 in the preferred embodiment. This instrument tray 172 is arranged on a scale 174. The scale 174 firstly has a dedicated display unit 175. In addition, the scale 174 is connected to the data processing installation 154 via a second interface 176. This is indicated by an arrow 178 and can also be seen in FIG. 5.

The data processing installation 154 shown schematically in FIG. 5 is essentially identical to the data processing installation 14 in FIG. 2. In this case too, there is a first interface 180 for receiving the image data from the first camera 160. This is indicated schematically by an arrow 166. In addition, the data processing installation 154 also has an evaluation unit 182 and a database 184. The evaluation unit 182 can write data to the database 184 and can read data therefrom, as indicated by arrows 186 and 188. Further, the data processing installation 154 also has an optional control unit 190, which can likewise be supplied with data by the evaluation unit 182 for the purpose of controlling further appliances and devices. This is indicated by an arrow 192. The data processing installation 154 also has a connection 194 which can be used to set up a connection—not shown in more detail—to the display unit 170.

In contrast to the data processing installation 14, the data processing installation 154 additionally has the second interface 176. As already described previously, this is used to forward the data from the scale 174 to the evaluation unit 182. This is indicated schematically by an arrow 196.

If, as indicated in FIG. 4, instruments, in this case the pair of scissors 58 and the clamp 64, are now again placed into the instrument tray 172 as a finished set of instruments, the scale determines the weight of this set of instruments. This is preferably accomplished by operating a push-button 198. The weight of the set of instruments preferably means the total weight thereof. This is preferably accomplished following prior taring of the scale with the instrument tray 172 in order to compensate for unevennesses in the weights of the instrument trays used.

The weight data obtained in this way are then forwarded via the second interface 176 to the evaluation unit 182 of the data processing installation 154. There, they are compared with the nominal weight of the present set of instruments comprising the pair of scissors 58 and the clamp 64. Said nominal weight is stored as a reference in the database 184. If the ascertained weight of the pair of scissors 58 and the clamp 64 matches the stored nominal weight, the data processing installation 154 provides the user with an appropriate notification via the display 170.

If the ascertained weight differs from the stored nominal weight after consideration of any tolerances, however, the user is notified of this as a fault in the set of instruments via the display unit 170.

The user then needs to check the allegedly complete set of instruments once again. Possible faults in this context may be incorrect transfer of the instruments from the instrument analysing unit to the coarse identification unit and faults particularly in the assembly of more complex instruments. By way of example, single internal parts may be missing. This cannot be identified from the outside and is therefore not a simple matter for the user to ascertain.

The reference weight or nominal weight of a respective set of instruments may be stored in the database 184 in different ways. One option in this context is for the individual weights of the respective instruments to be stored. These would then each be recalculated by the data processing installation 154 for each appropriate set of instruments and would then be compared with the ascertained weights accordingly. Alternatively, it is also possible to determine nominal weights for complete sets of instruments and hence for said nominal weights to be stored for each set of instruments as a fixed value in the database 184.

The nominal or reference weights of the instruments or sets of instruments are determined either by including manufacturer data in the data processing installation 154 or by means of proprietary weighing in a learning phase. The latter case preferably involves the performance of a plurality of weighing operations with the respective (sets of) instruments, as a result of which, particularly under different ambient conditions such as humidity and temperature, there are a plurality of weights for an instrument or set of instruments. This means that it is then possible to ascertain and store an appropriate fault tolerance using the standard deviation.

Besides the previously shown refinement of the device 100 and 150 with the coarse identification units 106 and 156, FIG. 6 shows a further preferred embodiment in the form of a coarse identification unit 200.

Even though the coarse identification unit 200 is shown as a single element in this case, it goes without saying that it can be combined in any form with the previously shown instrument analysing units 12, 102 and 152.

The coarse identification unit 200 can be regarded as a combination of the coarse identification units 106 and 156.

The coarse identification unit 200 has a further camera 202 which is arranged on a stand 204. The arrangement of the further camera 202 is similarly such that it is arranged above a second support 206 and is oriented such that the camera perspective is directed onto this second support 206. The second support 206 also has a scale 208. This scale 208 has an instrument tray 210 arranged on it. Both the further camera 202 and the scale 208 are connected to a data processing installation 212, as indicated schematically by arrows 214 and 216.

Figure 7:
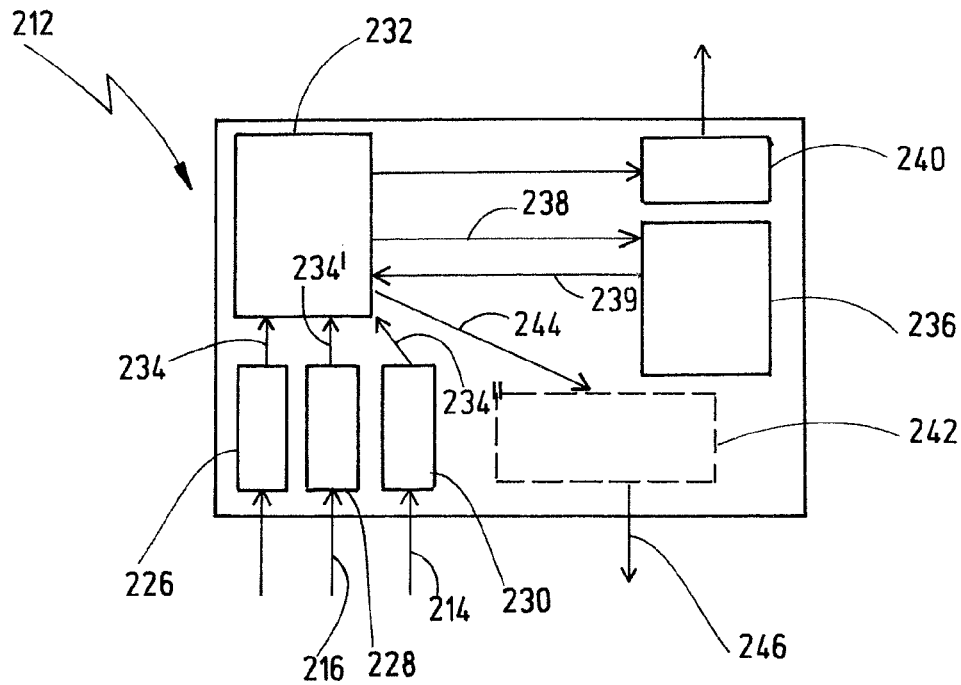
FIG. 7 shows a schematic representation of a data processing installation for an overall device with a coarse identification unit as shown in FIG. 6.

The data processing installation 212 is otherwise of a design similar to the previously described data processing installations 14, 104 and 154 and is described in more detail in conjunction with FIG. 7. It is otherwise connected to a display unit, which is not shown in FIG. 6 for the sake of clarity.

In addition, the scale may also be connected to a dedicated display unit 218, as indicated schematically by an arrow 220. The display unit 218 is then used to display the respective weight of the objects arranged on the scale 208.

In order to trigger the image capture and weighing operations, the further camera 202 and scale 208 are actuated by push-button in this case too, as indicated schematically by arrows 222 and 223. This can be accomplished by separate individual push-buttons or, as shown in FIG. 6 in this case, can be effected by a shared push-button 224.

The coarse identification with the coarse identification unit 200 is essentially similar to the previously described coarse identifications with the coarse identification units 106 and 156. One difference from the previously described coarse identification in this context, however, is the possibility of simultaneous identification using the further camera 202 and the scale 208.

This embodiment has the advantage that it is firstly possible to detect faults in the assembly of more complex instruments on the basis of a weight difference, while the visual individual key features of the respective instruments are nevertheless still able to be checked. This means that it is possible to ensure that each of the provided instruments in the set of instruments has actually been arranged in the instrument tray 210 and is correctly assembled.

In order to be able to receive these data, the data processing installation 212 now has a second interface 228 and a third interface 230 besides a first interface 226. This can be seen in FIG. 7 in particular. All the interfaces 226, 228 and 230 forward their data to an evaluation unit 232, as indicated by arrows 234, 234' and 234". The evaluation unit 232 can now interchange the data obtained in this manner with a database 236 and compare them with the reference data from this database 236. This is indicated schematically by arrows 238 and 239. Hence, besides the image data from the respective instrument analysing units, the evaluation unit 232 can also compare the image data from the coarse identification unit 200 and the weighing data from the coarse identification unit 200 with appropriate reference data.

Further, the data processing installation 212 also has a connection 240 for outputting the data to a display unit—not shown in more detail. The data processing installation 212 may also be provided, again optionally, with a control unit 242 in order to control appropriate devices or units on the basis of the evaluated data. In this case, the transmission of the data from the evaluation unit 232 to the control unit 242 is indicated by an arrow 244. The actuation of external units and devices is indicated by an arrow 246.

Figure 8:
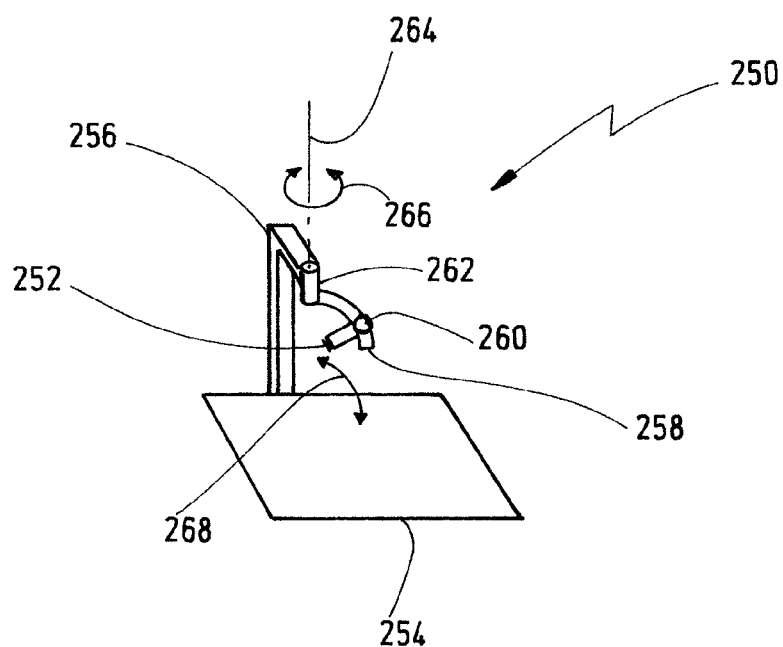
FIG. 8 shows a schematic perspective representation of a camera arrangement for instrument and coarse identification units with an alterable perspective.

FIG. 8 shows a camera arrangement 250. The configuration of this camera arrangement 250 can be transferred to the respective instrument analysing units 12, 102, 152 or coarse identification units 106 and 200 as appropriate.

The camera arrangement 250 has a camera 252, which is likewise arranged above a support 254. The camera 252 is arranged above the support 254 by means of a stand 256. In this case, the camera arrangement 250 is such that the position of the camera 252 is arranged so as to be alterable and, in this context, the camera 252 can cover a hemispherical surface area of dedicated positions. In this case, the camera 252 is arranged such that it always has its camera perspective oriented in the direction of the support 254.

In the present example, this is achieved by virtue of the stand 256 having a bow 258. Said bow 258 has the camera 252 arranged on it so as to be able to move along said bow 258. By way of example, this movement or else arrangement can be effected by a motor 260, which is shown schematically in this case. For its part, the bow 258 has one end arranged on the stand 256 via a second motor 262.

The bow 258 can therefore subsequently make rotations about an axis 264 of the motor 262, as indicated by a double-headed arrow 266. Similarly, the camera 252 can be moved along the bow 258 by the motor 260, as indicated by a double-headed arrow 268.

Ultimately, this configuration of a camera arrangement 250 allows for the respective instrument and coarse identification units to provide image data or snapshots from two or an arbitrary number of different perspectives.

Figure 9:
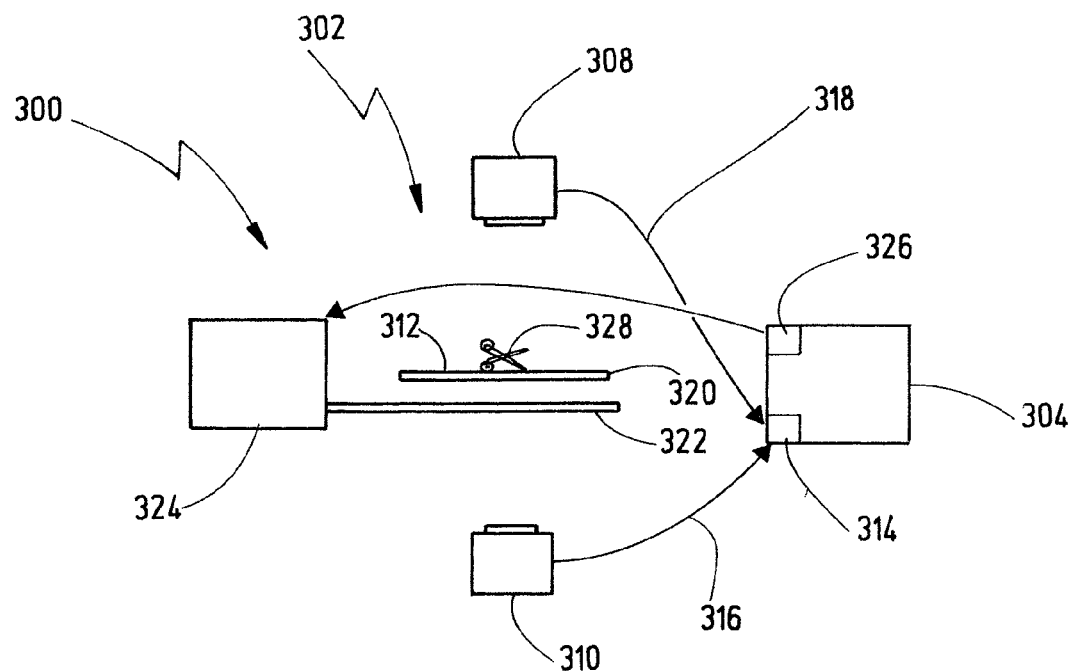
FIG. 9 shows a schematic side view of a device according to the present invention with an instrument analysing unit having a first and a second camera and an enhanced-contrast background below the instrument that is to be identified.
Figure 10:
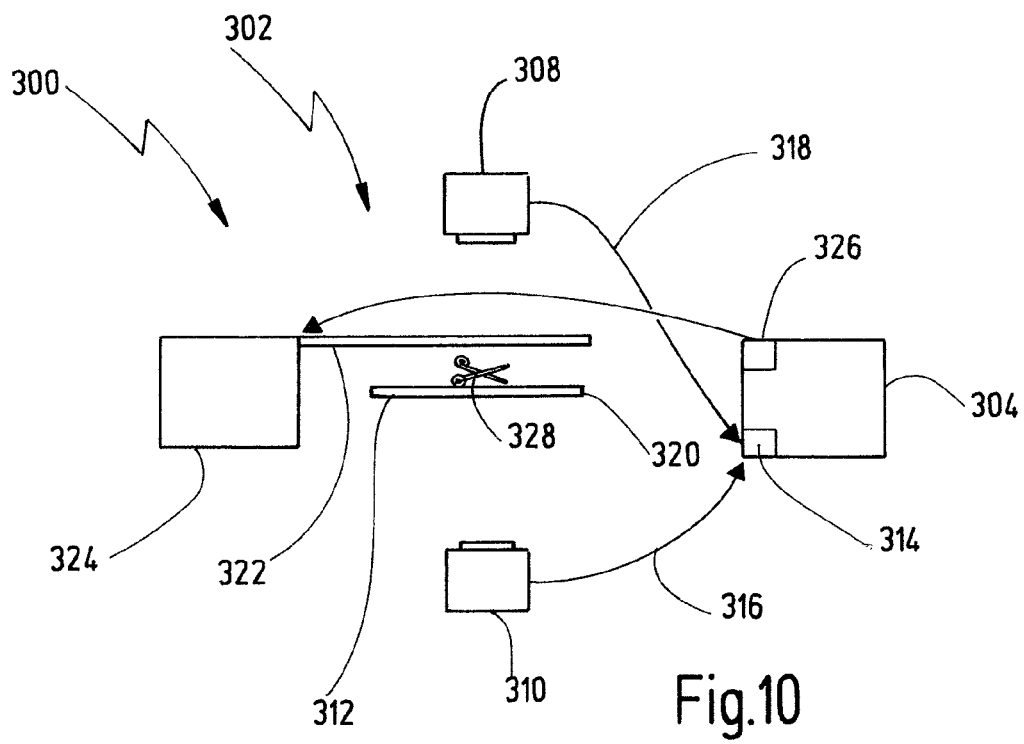
FIG. 10 shows a schematic side view of a device according to the present invention with an instrument analysing unit having a first and a second camera as shown in FIG. 9, with a contrast-enhancing background above the instrument that is to be identified.

FIGS. 9 and 10 show a further device 300 according to the present invention. The device 300 has an instrument analysing unit 302, a data processing installation 304 and optionally a coarse identification unit, the latter not being shown in more detail for the sake of clarity. This coarse identification unit is configured in the same way as one of the coarse identification units 106, 156 or 200 already shown and explained before.

Besides a first camera 308, the instrument analysing unit 302 additionally has a second camera 310. The first camera 308 and the second camera 310 are arranged relative to one another such that they are respectively arranged on one side of a support 312 of the instrument analysing unit 302.

Both cameras 308 and 310 are connected to the data processing installation 304 via a first interface 314 which is indicated schematically in this case. This is indicated schematically by arrows 316 and 318.

In the present exemplary embodiment, the support 312 has a transparent base area 320 and also a contrast-enhancing background 322.

In this case, the transparent base area 320 may be made from any transparent materials. These merely need to allow appropriate snapshots to be taken and instruments to be placed onto said base area 320. Examples which may be mentioned for these materials are glass or transparent plastics, such as Plexiglas.

In this context, the contrast-enhancing background 322 is in the form of a moving unicoloured plate. In addition, the contrast-enhancing background 322 is arranged on a movement unit 324. This movement unit 324 is able to transfer the contrast-enhancing background 322 from a position beneath the transparent base area 320 to a position above the transparent base area 320—in each case in reference to the illustration in FIGS. 9 and 10. This can be effected by means of rotation or by means of a motion sequence of the type lateral displacement, raising and movement back again, for example. It is likewise conceivable to have an arrangement on roller conveyors—which is not shown in this case—which run beside the transparent base area 320 and allow the contrast-enhancing background 322 first of all to be displaced laterally beside the transparent base area 320 and to have its vertical height adjusted so that it can then subsequently be pushed back above or below the transparent base area 320 again.

Further, the movement unit 324 is connected to a control unit 326—likewise indicated only schematically in this case—of the data processing installation 304.

As has already been explained as an option in the previously described exemplary embodiments of the data processing installations, this control unit 326 receives information and signals from an evaluation unit—not shown in more detail here—of the data processing installation 304 and therefore, in this case, controls the displacement and adjustment of the contrast-enhancing background 322 by means of the movement unit 324.

For the purpose of complete automation, it would also be conceivable for the control unit 326 in this case also to control the triggering of the first camera 308 and the second camera 310 and the associated capture of the image data.

With regard to the operation of capturing the image data from a respective instrument, a pair of scissors 328, that is indicated schematically in this case, the first camera 308 first of all captures an image of the pair of scissors 328. In this case, the contrast-enhancing background 322 is arranged beneath the transparent base area 320 such that it has a positive influence on the image capture properties by virtue of it increasing the contrast between the instrument to be examined, in this case the pair of scissors 328, and the background.

Next, when the image data have been received in the data processing installation 308, the control unit 328 is used to displace the position of the contrast-enhancing background 322 by means of the movement unit 324. This involves said background 322 being brought from beneath the transparent base area 320 into a position above the transparent base area 320. This is comprehensible from the transition from FIG. 9 to FIG. 10.

When the contrast-enhancing background 322 has been positioned, the second camera 310 can now begin to capture the image data. In this context, said second camera 310 can capture the image data from the lower side—with reference to the illustration of FIG. 10—of the pair of scissors 328 through the transparent base area 320. In this case too, the contrast-enhancing background 322 again ensures a sufficient difference between the instrument to be examined and the background in order to facilitate image capture and subsequent examination for anomalies.

Even though the description of this method has been provided in this order, it is also possible to reverse the order, i.e. to capture first of all the underside and then the top of a pair of scissors 328 in the form of image data.

The image data received in this manner from a first camera 308 and a second camera 310 are then transmitted to the data processing installation 304 and evaluated in the evaluation unit—which is not shown in more detail in this case—of the data processing installation 304 in line with the explanations provided before. As a result, the instrument, in this case the pair of scissors 328, is examined and is analysed for any anomalies.

Figure 11:
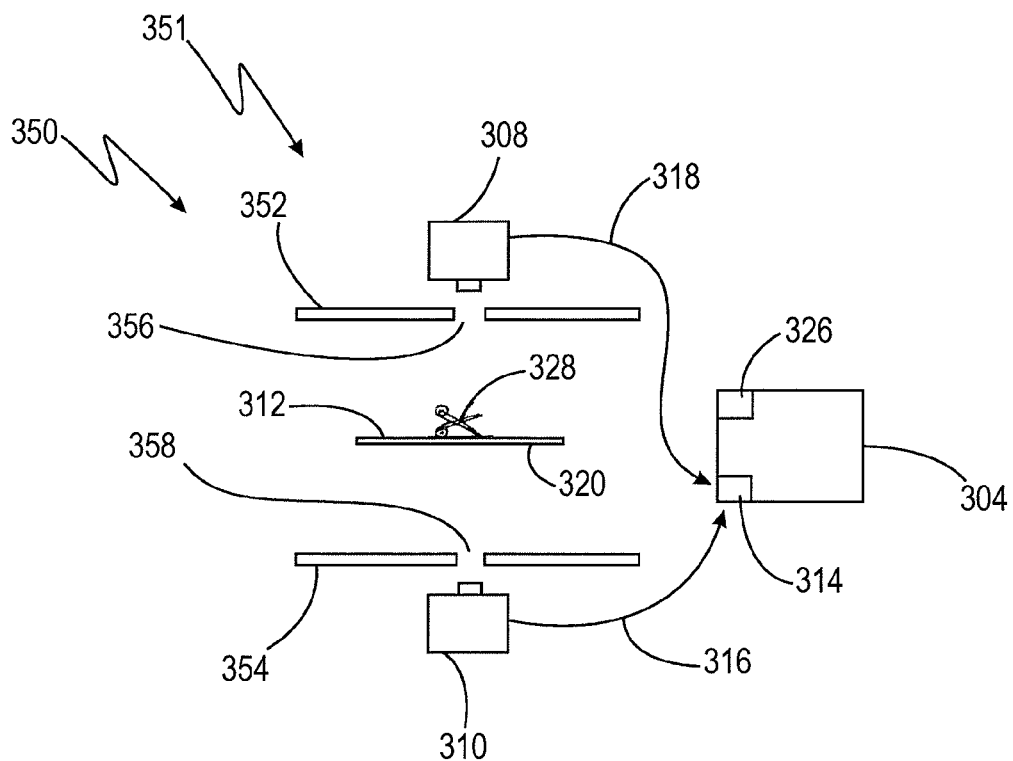
FIG. 11 shows a schematic side view of a further device according to the present invention with an instrument analysing unit analogue to the device of FIGS. 9 and 10, having two contrast-enhancing backgrounds.
Figure 12:
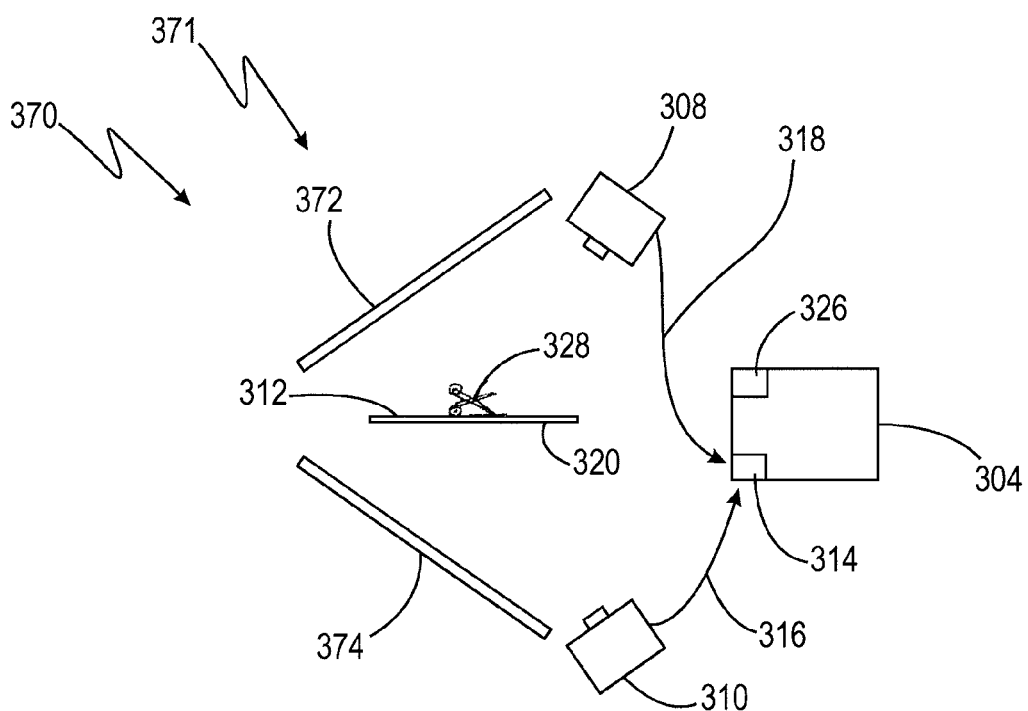
FIG. 12 shows a schematic side view of a further device according to the present invention with an instrument analysing unit analogue to the devices of FIGS. 9, 10 and 11, having two contrast-enhancing backgrounds as well.

Further devices 350 and 370, as shown in FIGS. 11 and 12, comprise partly identical features as the device 300 of FIGS. 9 and 10. Accordingly, identical features are designated by the same reference numerals and are not described in more detail below. Although not shown in FIGS. 11 and 12 for the sake of clarity, the devices 350 and 370 do, similar to device 300, also optionally comprise a coarse identification unit. This coarse identification unit is configured in the same way as one of the coarse identification units 106, 156 or 200 already shown and explained before.

In contrast to the device 300 of FIGS. 9 and 10, the device 350 of FIG. 11 comprises an instrument analysing unit 351 with two contrast-enhancing backgrounds 352 and 354. These are respectively arranged each on one side of the support 312. Therein, these contrast-enhancing backgrounds 352 and 354 are respectively located between the support 312 and the respective camera 308, 310. In order to allow the capture of image data of the instruments arranged on the support 312, that is to say on the transparent base area 320, the contrast-enhancing backgrounds 352 and 354 each comprise an opening 356, 358. The cameras 308 and 310 may then capture images of an instrument, e.g. the pair of scissors 328, arranged on the transparent base area 320, through these openings 356 and 358. Therein, the respectively opposite contrast-enhancing background 352 and 354 aids in enhancing the image capture properties, as mentioned before.

With respect to the representation of FIG. 11, the contrast-enhancing background 352 serves as a background for image captures with camera 310, whereas the contrast-enhancing background 354 serves as the background for image captures with camera 308. The possible image capturing of the respectively opposite camera 308 or 310 and of the respective opening 356 or 358 may be considered in the image processing, e.g. by being removed from the image data. This may be done, for example, by using image subtraction, meaning via images taken with and without an instrument. With the device 350 simultaneous and, in the consequence, time saving image captures are possible due to the fixed arrangement of cameras 308 and 310 and of contrast-enhancing backgrounds 352 and 354. A time consuming rearrangement and/or reorientation of camera and/or contrast-enhancing background is not necessary.

The device 370 as shown in FIG. 12 comprises an instrument analysing unit 371 with two contrast-enhancing backgrounds 372 and 374, as well. In contrast to the device 350 of FIG. 11 these contrast-enhancing backgrounds 372 and 374 are inclined with respect to a theoretical plane provided by the support 312 or the transparent base area 320. This orientation of the contrast-enhancing backgrounds 372 and 374 is such that they may serve as a respective background for the cameras 308 and 310 for also enhancing the image capture properties. For this, the arrangement of cameras 308 and 310 is such that their respective perspective lies also inclined with respect to the aforementioned plane. The configuration shown in this embodiment allows for the image capturing of the pair of scissors 328 with the camera 310 being done in front of the contrast-enhancing background 372, for example. In the same way, the image capturing of the pair of scissors 328 with the camera 308 may be done in front of the contrast-enhancing background 374. Camera 308 and 310 are arranged respectively on the side of the contrast-enhancing backgrounds 372 and 374. Therefore, the contrast-enhancing backgrounds 372 and 374 do not require an additional opening as it is the case for the contrast-enhancing backgrounds 352 and 354 of the device 350. This is due to the inclined arrangement, which avoids the need for capturing the images through the contrast-enhancing backgrounds. In the consequence, also an additional step in processing the image data is not necessary, since the camera 308 or 310 and the respective opening is not a part of the captured image data.

This embodiment has also the advantage that a simultaneous image capture with both cameras 308 and 310 is possible without any delays since a rearrangement and readjustment of the background and/or the camera is not necessary. For this, camera 308 and 310 as well as contrast-enhancing backgrounds 372 and 374 are also preferably fixedly arranged.

It goes without saying that the explanations provided previously with regard to the configuration of a camera, in particular in FIG. 8, can also be transferred to the cameras 308 and 310 shown here in FIGS. 9, 10, 11 and 12. In addition, it also goes without saying that appropriate lighting units are provided in this device and are not shown in more detail merely for the sake of simplification and clarity in the illustrations. Besides the previously illustrated use of lamps, it is further also conceivable for the cameras 308 and 310 shown here, and also for all other cameras and camera devices described before, to contain lighting devices in or on the camera itself. This results in a compact space-saving arrangement.

Besides the previously described use of the instrument analysing units 12, 102, 152, 302, 351 and 371 for the purpose of examining the instruments placed on the respective supports for anomalies, one preferred embodiment of the present invention may also have provision for the respective data processing installations 14, 104, 154, 212 and 314 to be configured such that they also allow identification of the instruments that have been placed onto said supports. By way of example, this identification of the instruments can be effected by using specifically coordinated object identification algorithms, such as correlation methods and methods of edge-based object identification (e.g. generalized Hough transformation), which identify individual objects, i.e. in this case the instruments that have been placed onto said supports, using the captured image data.

To this end, the respective databases may then store appropriate reference images with which the respective evaluation units can compare the identified instruments.

The instruments recognized and identified are then compared with packing lists which are likewise preferably stored in the data processing installation and on which the instruments which belong to an instrument set that is to be packed appear.

It is thus advantageously possible, in addition to working through packing lists on the basis of object identification for the purpose of assembling sets of instruments, to simultaneously examine the instruments that have been placed onto the supports for any type of anomalies in accordance with the present invention.

The aforementioned examination of the instruments for anomalies will now be explained by way of example below with reference to FIGS. 13 to 15 for the device according to the present invention and for the method.

Figure 13:
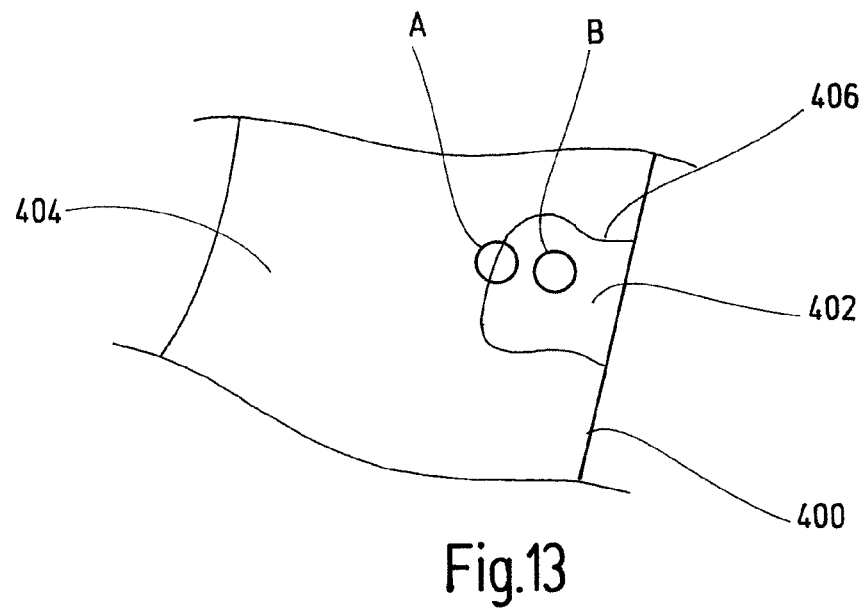
FIG. 13 shows an enlarged schematic detail representation of a medical instrument having an anomaly.
Figure 14:
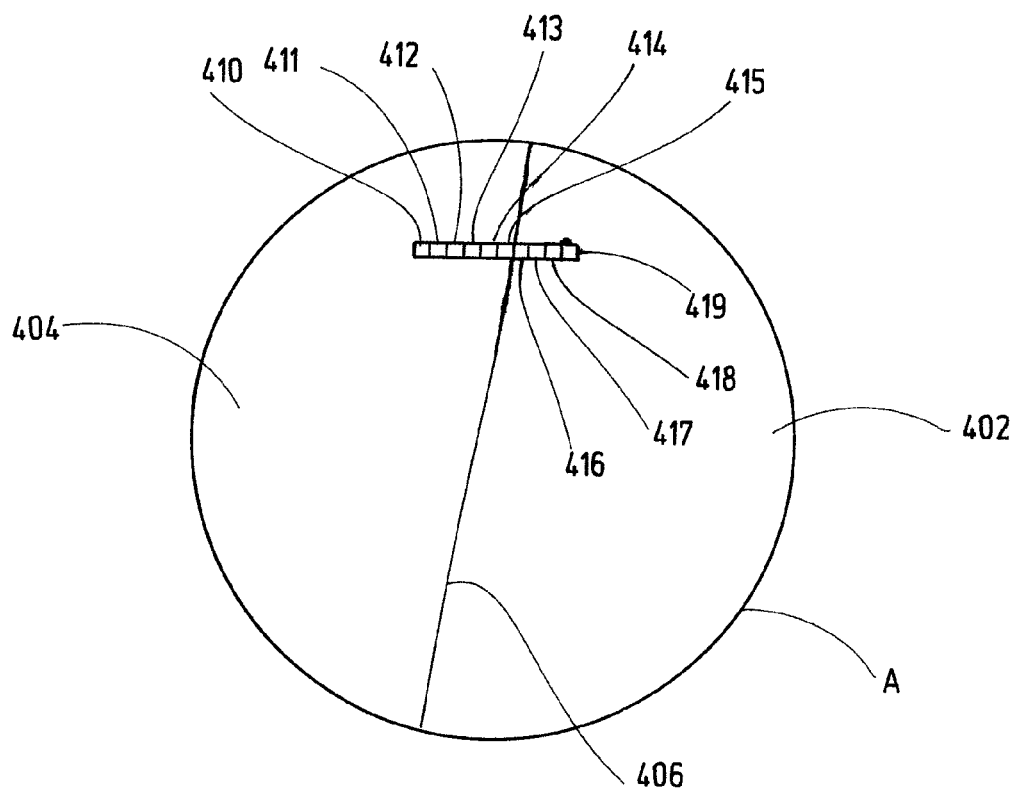
FIG. 14 shows a greatly enlarged schematic representation of the circle A from FIG. 13.

The detail from an instrument 400 that is shown in FIG. 13 may be the detail from the grip of the aforementioned pair of scissors 58 or 328 or the clamp 64, for example.

In the detail indicated here, this instrument 400 has an anomaly 402 beside an undamaged area 404. Theoretically, this anomaly 402 may firstly be a regular part of the instrument, such as a grip, a sleeve, a rivet in a different kind of colour or the like. In addition, however, it may also be a damaged area, as is assumed for this example. Damaged areas may include corrosion, such as stress, surface area, contact or friction corrosion or the like, soiling, e.g. by organic residues, or other discolourations. For the explanations which follow, it is assumed by way of example that the anomaly 402 is corrosion.

In addition, it is assumed for the explanations which follow that the anomaly 402 and the undamaged area 404 are separated from one another by an explicit transition 406. Such a transition 406 is not necessary for the mode of operation of the devices according to the present invention and the method and will often also not appear in reality. In the present case, it is merely used to illustrate the invention using the example in FIG. 13 as clearly and simply as possible.

In order to examine the instrument 400 for any anomalies, the instrument is first of all placed onto a support, for example the support 16 of the device 10, and the first camera 18 is used to capture the image data from said instrument 400. These image data are then examined by the evaluation unit 26 for regions which have anomalies.

In this case, this examination and analysis of the image data from the instrument first involves a search for regions of conspicuous colour. In the present exemplary embodiment, this search for regions of conspicuous colour is effected such that the colour intensity of each pixel of the received image data is determined. This first of all involves using the contrast-enhancing background 66 to filter the background out of the image data so as to obtain merely the pure image data from the instruments to be examined or, in this case, the instrument 400 to be examined.

In the present exemplary additive RGB colour space, the colour intensity is then determined such that the respective differences between the individual image channels are determined. This can be accomplished by using formula 1 below, for example:

$$FS(x, y) = \frac{|BK_1(x, y) - BK_2(x, y)| + |BK_2(x, y) - BK_3(x, y)| + |BK_3(x, y) - BK_1(x, y)|}{3} \quad \text{Formula 1}$$

This formula relates to the colour intensity for a single pixel having the coordinates (x, y) in a raster graphics system. In this case, FS denotes the colour intensity and $BK_i(x,y)$ denotes the respective image channel value in one of the three image channels (where i=1, 2 or 3) of the pixel at the location (x,y) in the RGB colour space. Within the context of the present example, each image channel represents one of the channels of the RGB data, i.e. one of the colour values for red, green and blue. In relation to the medical instruments that are present, a frequently occurring undamaged metallic surface would then have very high values in all three available image channels. According to formula 1, this would result in the individual terms between the absolute value signs becoming very small or zero as a result of the almost identical values in the individual image channels. The result is a low value for the colour intensity FS(x,y).

As another alternative, there may also be a frequently occurring black plastic part of the medical instrument, which would then have very low values in each individual image channel. This would also involve the individual terms in the absolute value signs again becoming very small or zero, due to the similarity among the individual values in the respective individual terms, and therefore the value for the colour intensity FS(x,y) also becoming very low.

If there is now the situation of an anomaly, such as the anomaly 402 in the form of corrosion, much more different image channel values arise in the individual image channels. In this regard, it shall be assumed that corresponding corrosion is coloured such that it has a distinct red component but relatively small green and blue components. In relation to the image channels of the RGB colour space, this then means that, in this example, one image channel has a distinctly higher value than the other two image channels. With reference to formula 1, the result of this is then that, when the other two image channels have a very high degree of similarity, the difference-forming term for these two image channels becomes small or almost zero. By contrast, the other two remaining terms, which comprise the image channel with the high value and are being compared with the remaining two other image channels, assume relatively large values. As the result of formula 1, this then leads to a comparatively high value for the colour intensity FS.

In order to distinguish small colour deviations in the form of differences between the image channels, on the one hand, from regions which are actually of conspicuous colour, on the other hand, particularly anomalies, the method according to the present invention and the device according to the present invention are preferably provided with a threshold value which the colour intensity FS according to formula 1 must exceed. Only in this way is the colour deviation categorized as an anomaly, that is to say a region of conspicuous colour. This threshold value is ascertained and determined empirically on the basis of the medical instruments used, i.e. by means of experiments with a series of medical instruments from the stock of medical instruments used.

In this context, it should be noted that this threshold value does not have to be determined permanently for the entire operation of the device and the method according to the present invention. It can also change in the course of operation and application of the method on the basis of adjustments by the user. By way of example, this is expedient when new instruments are added to the stock which shall be examined using the device according to the present invention and the method. It is also suitable when the instruments used are inherently subject to slight basic discolouration and it therefore becomes necessary to adjust the threshold value. It likewise also comes into consideration when, for some other arbitrary reason, it is necessary to boost (reduction of the threshold value) or reduce (increase of the threshold value) the sensitivity of the device or the method.

The distinction between the undamaged area 404 and the anomaly 402 will now be described in more detail below with reference to the enlarged illustration in FIG. 14. In this case, this greatly enlarged detail from the instrument 400 shows the transition area from the undamaged area 404 to the anomaly 402 by means of the transition 406. In this context, individual pixels 410 to 419 are schematically indicated. Of these, the pixels 410 to 415 fall into the undamaged area 404, while the pixels 416 to 419 fall into the area of the anomaly 402. It goes without saying that the image data as a whole are present as a collection of pixels, which means that the series of ten pixels 410 to 419 that is shown here merely serves to illustrate the mode of operation of the device and the method, and it has been dispensed with showing all pixels, which would ultimately fill all of the illustrations, for the purpose of clarity.

The present invention would then involve examining the respective colour intensity of the pixels shown here in the next step.

This would result in a comparatively low value for the colour intensity FS being ascertained for all pixels 410 to 415. In line with the explanation provided before, the reason for this is that the undamaged area 404 is metallic in the present example, which means that all image channels have very high values. In line with formula 1, this results in the total value FS turning out to be low. The colour intensities of the pixels 410 to 415 from the undamaged area 404 are therefore also below the threshold value. Accordingly, the present invention would involve this undamaged area 404 also being identified as such an area without a region of conspicuous colour and therefore without faults or damage.

The further pass of the pixels would then result in a different outcome for the colour intensity FS in the case of the subsequent pixels 416 to 419 illustrated by way of example here. Using the previously mentioned example of corrosion, it would be the case here that very high values are to be expected in one image channel while the other image channels would have comparatively low values. With reference to the explanations provided previously, this then results in a high value being achieved for the colour intensity FS according to formula 1, said high value being above the threshold value.

Hence, each of the pixels 416 to 419 is provided with a grading which can be denoted as being of conspicuous colour.

Next, the invention then involves all pixels situated in the area of the anomaly 402 being combined to form a group. This group then comprises adjacent pixels of conspicuous colour. In addition, this group then describes a region of conspicuous colour, namely the anomaly 402.

When all of the pixels associated with the anomaly 402 have been found, the user is then notified that the instrument 400 being examined has an anomaly 402. In addition, it is also conceivable for the device according to the present invention to have further devices, such as robots, which then remove such an instrument having an anomaly 402. Such devices are not shown in more detail in this case, however.

In one preferred embodiment of the present invention, the procedure with the device and the method then continues such that the anomaly 402 found is also identified.

To this end, this region of conspicuous colour in the form of the anomaly 402 is classified. In this regard, the data processing installation 14, particularly the database 28, stores the various classes of regions of conspicuous colour, that is to say anomalies, that can arise.

This storage in the data processing installation 14 may already have been included as a preset by the manufacturer of the device, for example. Preferably, this collection of classes is learnt using the system in the form of the device and the method, however. To this end, a series of instruments that are used is examined by the system in succession and all regions of conspicuous colour that are identified as anomalies are indicated to the user. During this learning phase, the user then himself examines the instruments with these identified anomalies and associates them with particular classes. This can be accomplished by means of input using the keyboard 54, for example.

The classes produced or input and associated in this manner may comprise both damage and soiling and also instrument parts of different colour, such as coloured grips.

For each determined class, a colour distribution is then obtained from the pixels that arise in the anomalies with the various colour information from said pixels. In the three-dimensional RGB colour space described here by way of example, this colour distribution is in the form of a 3D histogram.

This 3D histogram usually has partly uneven profiles which can optionally be revised by convolution with a 3D Gaussian function to produce smoother probability functions for the class-specific colour distributions.

Finally, the 3D histogram obtained in this manner can then be used to determine a probability for each piece of colour information present in the form of the three image channels. Since each 3D histogram is different for each class in the device according to the present invention, there also arise, for a piece of colour information which is identified or results from an image pixel, conditional probabilities—which are different for each of these classes—of such a piece of colour information for belonging to or for being able to be associated with a relevant class.

This aforementioned piece of colour information can be regarded as a transformation $\vec{F}$ for the pixel (x,y) into the RGB colour space:

$$\vec{F}(x,y) = (r,g,b) \qquad \text{Formula 2:}$$

On the basis of the previously presented learning phase, it is possible to ascertain what is known as an a priori probability $Pr(C_i)$, which is the probability of a relevant class $C_i$ arising from statistical perspectives in relation to all available classes.

Overall, the probability of a pixel belonging to a particular class is then determined using the a posteriori probability shown below in formula 3:

$$\text{a\_posteriori}_i(C_i \mid \vec{F}) = \frac{P_i(\vec{F} \mid C_i) \cdot Pr(C_i)}{\sum_{i=1}^{N} P_i(\vec{F} \mid C_i) \cdot Pr(C_i)} \qquad \text{Formula 3}$$

In this case, $C_i$ is a class from the set of all classes C which are stored in the database, $\vec{F}$ is the transformation for the pixel x, y into the RGB colour space, also called colour value (or colour information before), and $Pr(C_i)$ is the a priori probability—described above—for the occurrence of the class $C_i$ per se. The expression $P_i(\vec{F}|C_i)$ is the class-related probability ("likelihood"). This indicates the probability of a colour value or a piece of colour information arising specifically in the class $C_i$. In this regard, the class-related collection of colour values $\vec{F}$ can be used to determine a (smoothed) histogram during a training phase for each class $C_i$. This histogram then indicates the probability of a colour value $\vec{F}$ belonging to a specific class $C_i$.

In its general form, this formula 3 is also known as Bayes' formula and is based on Bayes' theorem.

Figure 15:
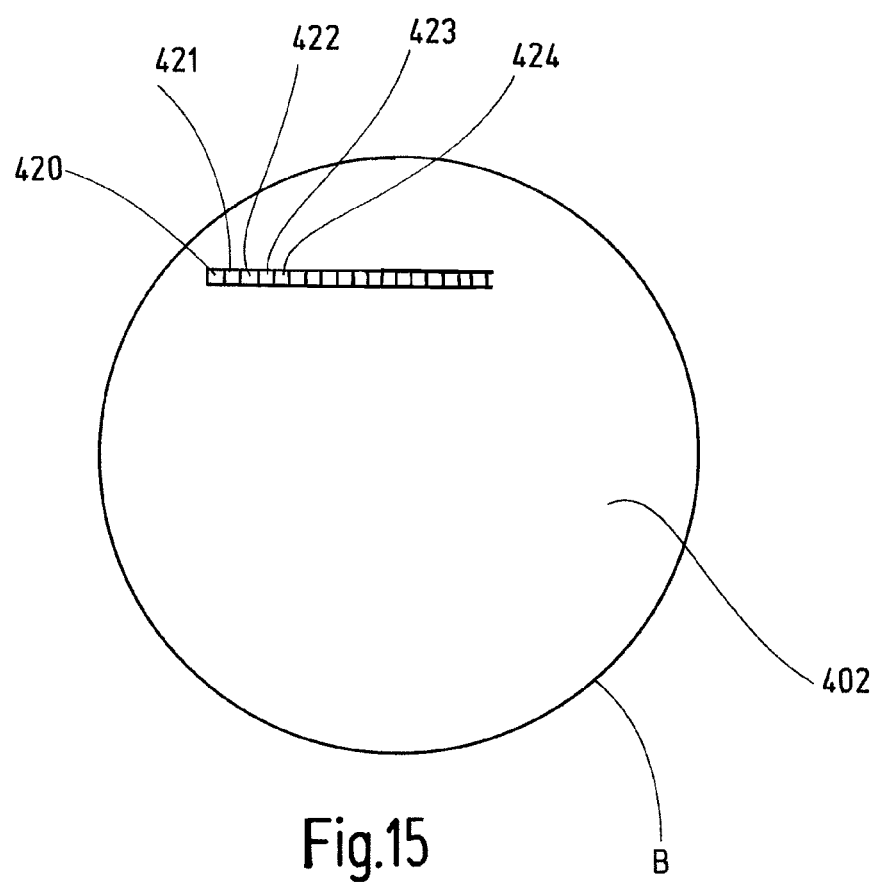
FIG. 15 shows a greatly enlarged schematic representation of the circle B from FIG. 13.

The illustration in FIG. 15 shows a few image pixels by way of example, in this case exclusively for the anomaly 402, with exclusively the pixels 420 to 424 being provided with reference numerals in this case.

In line with the previously presented formula 3 for determining the a posteriori probability of a pixel belonging to a particular class $C_i$ on the basis of the colour information that is obtained from said pixel, the relevant a posteriori probability for each class that is available in the system of the data processing installation 14 is respectively ascertained for each of the pixels 420 to 424.

So as now to associate a pixel with a class, for each pixel 420 to 424 the respectively greatest probability, that is to say the maximum of the a posteriori probabilities, is ascertained over all classes. This is illustrated by formula 4 below:

$$c_{MAP}(\vec{F}(x,y)) = \underset{c \in C}{\text{argmax}}\, \text{a\_posteriori}(c \mid \vec{F}(x,y)) \qquad \text{Formula 4}$$

In this case, c is a class from the set of all classes C. MAP means Maximum A Posteriori. $c_{MAP}$ is therefore the class having the greatest a posteriori probability, which is then associated with the respective pixel.

In relation to the whole anomaly 402, this thus means that the respective class having the greatest probability $c_{MAP}$ is ascertained for all pixels 420 to 424 shown and for all remaining pixels from the anomaly 402 which are not denoted and shown in more detail here. However, since it may now arise that, by way of example, the class $C_1$ is ascertained for the pixel 420 and the class $C_2$ is ascertained for the pixel 421, a maximum will also be ascertained among all the pixels from the anomaly 402.

This is accomplished by determining the most frequently occurring class from the set of all available pixels from the anomaly 402. This is illustrated by formula 5 below:

$$c_{anomaly} = \underset{c \in C}{\operatorname{argmax}} \sum_{j=1}^{M_{anomaly}} c_{MAP}(\vec{F}(x,y)_j)$$ Formula 5

In this case, $c_{anomaly}$ is the most probable classification of the discovered anomaly 402 to a class, and $M_{anomaly}$ is the number of all pixels in the examined anomaly, in this case the anomaly 402.

Following identification and assignment of this class $c_{anomaly}$ to the region of conspicuous colour that has been found in the form of the anomaly 402, the user is notified of the class, i.e. the kind of anomaly. This can be accomplished for example by the display unit 38.

Alternatively, it is also conceivable for further devices in this case likewise to be present as part of the device according to the present invention, said devices then processing a relevant instrument 400, which has an anomaly 402 that is now classified by $c_{anomaly}$, further accordingly. This processing may firstly be supplying it to further cleaning and sterilization steps, for example if the anomaly 402 is organic residues or soiling in general. The class $c_{anomaly}$ would then be a class from the group of soilings.

Alternatively, the instrument 400 can also be delivered for repair or for rejection from the stock if the identified anomaly 402 is damage, e.g. corrosion. The class $c_{anomaly}$ would then belong to the damage classes.

Such a device for further processing of these instruments may be a robot, for example. This robot could then further also be actuated by the data processing installation 14 within the context of the present invention. The control unit 44 mentioned previously as an option is suitable for this purpose.

Even though the method according to the present invention and the device have been described above with regard to the identification of anomalies and regions of conspicuous colour in connection with the device 10, it goes without saying that the explanations provided before can also be transferred analogously to the other previously mentioned devices 100, 150, 300, 350 and 370.

In this connection, it should be noted that particularly an embodiment in line with the devices 300, 350 and 370 is preferred which allows the capture of image data from the top and underside from at least one respective perspective, preferably even from a plurality of perspectives in the case of combination with the camera arrangement 250. The reason for this is particularly that it allows the complete instrument 400 to be examined for anomalies without the need for action by a user in order to rotate or displace the instrument 400.

What is claimed is:

1. A device for identifying anomalies on medical instruments, comprising:
    a data processing installation; and
    an instrument analysing unit;
        said data processing installation having:
            a display unit,
            a database,
            a first interface, and
            an evaluation unit; and
        said instrument analysing unit having:
            a support, and
            at least one camera,
        wherein said at least one camera is arranged and oriented such that it can capture image data from medical instruments arranged on said support from at least one perspective, and
        wherein said data processing installation is designed such that
            it uses said first interface to receive image data from said at least one camera,
            it can store said received image data in said database,
            it can use said evaluation unit to examine said image data for regions which may have anomalies by finding regions of conspicuous colour,
            it can classify said regions of conspicuous colour,
            it can use said classification to determine whether said regions of conspicuous colour are respectively a regular part of the respective medical instrument or an anomaly,
            it can determine a type of anomaly when said regions of conspicuous colour are respectively determined to be an anomaly, and
            it can use a colour found in said regions of conspicuous colour to determine the type of anomaly.

2. The device of claim 1, wherein said anomalies are damage or soiling.

3. The device of claim 1, wherein said support has a contrast-enhancing background.

4. The device of claim 1, wherein said camera is arranged such that a position thereof can be altered, as a result of which it can capture said image data from at least two perspectives.

5. The device of claim 3, wherein said support has a transparent base area, and wherein said contrast-enhancing background is arranged such that a position thereof can be altered between the two sides of said transparent base area.

6. The device of claim 3, wherein said support has a transparent base area, and wherein the device comprises two contrast-enhancing backgrounds respectively arranged on opposite sides of said transparent base area, such that at least one contrast-enhancing background is arranged behind a medical instrument arranged on said support with respect to a respective perspective of said at least one camera.

7. A method for identifying anomalies on medical instruments with a device for identifying anomalies on medical instruments, the device comprising:
    a data processing installation and
    an instrument analysing unit;
        said data processing installation having:
            a display unit,
            a database,
            a first interface, and
            an evaluation unit; and
        said instrument analysing unit having:
            a support, and
            at least one camera,
        wherein said at least one camera is arranged and oriented such that it can capture image data from medical instruments arranged on said support from at least one perspective, and
        wherein said data processing installation is designed such that
            it uses said first interface to receive image data from said at least one camera,
            it can store said received image data in said database,
            it can use said evaluation unit to examine said image data for regions which may have anomalies by finding regions of conspicuous colour,
            it can classify said regions of conspicuous colour,
            it can use said classification to determine whether said regions of conspicuous colour are respectively a regular part of the respective medical instrument or an anomaly, it can determine a type of anomaly when said regions of conspicuous colour are respectively determined to be an anomaly, and it can use a colour found in said regions of conspicuous colour to determine the type of anomaly;

the method comprising the following steps:
- a) placing at least one instrument onto said support of said instrument analysing unit,
- b) capturing image data by said at least one camera,
- c) forwarding said image data to said data processing installation,
- d) analysing said image data for anomalies on the instrument, and
- e) communicating information about said anomalies to a user, wherein step d) comprises the following steps:
- aa) finding regions of conspicuous colour,
- bb) classifying said regions of conspicuous colour,
- cc) using said classification to determine whether said regions of conspicuous colour are respectively a regular part of the instrument or an anomaly,
- dd) determining a type of anomaly when said regions of conspicuous colour are respectively determined to be an anomaly, and
- ee) using a colour found in said regions of conspicuous colour to determine the type of anomaly.

8. The method of claim 7, wherein step aa) has the following steps:
- determining a colour intensity of each pixel,
- comparing said colour intensity with a predetermined threshold value,
- categorising a respective pixel as being of conspicuous colour if said threshold value is exceeded,
- combining all adjacent pixels of conspicuous colour to form a region of conspicuous colour.

9. The method of claim 8, wherein determining said colour intensity of each pixel is implemented by ascertaining a difference between image channel values of the respective pixel.

10. The method of claim 7, wherein step bb) has the following steps:
- ascertaining a probability for each pixel in a region of conspicuous colour of belonging to a particular class of anomalies,
- selecting the class having the highest probability and assigning this class to the respective pixel, and
- selecting the most frequently occurring class among the total number of all pixels in said region of conspicuous colour and assigning this class to said region of conspicuous colour.

11. A non-transitory computer-readable recording medium that stores therein a computer program product, which, when executed by a processor, causes the method according to claim 7 to be performed.

* * * * *